(12) United States Patent
Lee et al.

(10) Patent No.: US 6,496,715 B1
(45) Date of Patent: Dec. 17, 2002

(54) SYSTEM AND METHOD FOR NON-INVASIVE DETERMINATION OF OPTIMAL ORIENTATION OF AN IMPLANTABLE SENSING DEVICE

(75) Inventors: Brian B. Lee, Golden Valley, MN (US); Michael R. Kane, Shoreview, MN (US); Eric J. Panken, Edina, MN (US); James D. Reinke, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/718,689

(22) Filed: Nov. 22, 2000

Related U.S. Application Data

(63) Continuation-in-part of application No. 09/384,176, filed on Aug. 27, 1999, now Pat. No. 6,412,490, which is a division of application No. 09/033,678, filed on Mar. 3, 1998, now Pat. No. 5,987,352, which is a continuation-in-part of application No. 08/678,219, filed on Jul. 11, 1996, now abandoned.

(51) Int. Cl.$^7$ .................................................. A61B 5/04
(52) U.S. Cl. ....................................... 600/424; 600/509
(58) Field of Search .................................. 600/509, 424

(56) References Cited

U.S. PATENT DOCUMENTS

| | | | |
|---|---|---|---|
| 3,983,867 A | 10/1976 | Case | 128/2.06 G |
| 4,023,565 A | 5/1977 | Ohlsson | 128/2.06 B |
| 4,082,086 A | 4/1978 | Page et al. | 128/2.06 E |
| 4,170,227 A | 10/1979 | Feldman et al. | 128/704 |
| 4,223,678 A | 9/1980 | Langer et al. | 128/419 D |
| 4,263,919 A | 4/1981 | Levin | 128/708 |
| 4,407,288 A | 10/1983 | Langer et al. | 128/419 PG |
| 4,476,868 A | 10/1984 | Thompson | 128/419 PG |
| 4,523,707 A | 6/1985 | Blake, III et al. | 227/19 |
| 4,556,063 A | 12/1985 | Thompson et al. | 128/419 PT |
| 4,593,702 A | 6/1986 | Kepski et al. | 128/696 |
| 4,850,370 A | 7/1989 | Dower | 128/699 |
| 5,052,388 A | 10/1991 | Sivula et al. | 128/419 PG |
| 5,111,396 A | 5/1992 | Mills et al. | 364/413.06 |
| 5,226,425 A | 7/1993 | Righter | 128/710 |
| 5,231,990 A | 8/1993 | Gauglitz | 128/697 |
| 5,289,824 A | 3/1994 | Mills et al. | 128/696 |
| 5,313,953 A | 5/1994 | Yomtov et al. | 128/696 |
| 5,314,464 A | 5/1994 | Kenknight et al. | 607/132 |
| 5,331,966 A | 7/1994 | Bennett et al. | 128/696 |
| 5,333,616 A | 8/1994 | Mills et al. | 128/696 |
| 5,339,824 A | 8/1994 | Engira | 128/712 |
| 5,345,362 A | 9/1994 | Winkler | 361/681 |
| 5,365,935 A | 11/1994 | Righter et al. | 128/710 |
| 5,366,687 A | 11/1994 | Dalzell, Jr. et al. | 419/35 |

(List continued on next page.)

FOREIGN PATENT DOCUMENTS

| | | | |
|---|---|---|---|
| FR | 2107826 | 9/1971 | A61N/1/00 |
| WO | 9217241 | 10/1992 | A61N/1/365 |

OTHER PUBLICATIONS

Krahn, A. et al., "The Etiology of Synscope in Patients With Negative Tilt Table and Electrophysiological Testing" *Circulation*, 92:7 Oct. 1, 1995 pp. 1819–1824.

*Primary Examiner*—Carl Layno
(74) *Attorney, Agent, or Firm*—Girma Wolde-Michael; Michael C. Soldner

(57) ABSTRACT

A system and method for determining the optimal positioning of an implantable system for sensing physiologic signals within a body. According to a one embodiment of the system, electrodes are positioned on an external surface of a body, and an ECG monitoring device is used to measure cardiac signals between various pairs of the electrodes. One or more of the electrodes may be re-positioned until an electrode pair position and orientation is located that provides a maximum signal reading. This position and orientation may then be used as the position and orientation in which to implant a corresponding device.

45 Claims, 22 Drawing Sheets

U.S. PATENT DOCUMENTS

| | | | |
|---|---|---|---|
| 5,391,199 A | * 2/1995 | Ben-Haim | 607/122 |
| 5,404,887 A | 4/1995 | Prather | 128/772 |
| 5,411,031 A | 5/1995 | Yomtov | 128/706 |
| 5,417,717 A | 5/1995 | Salo et al. | 607/18 |
| 5,443,492 A | 8/1995 | Stokes et al. | 607/131 |
| 5,464,431 A | 11/1995 | Adams et al. | 607/4 |
| 5,464,434 A | 11/1995 | Alt | 607/6 |
| 5,511,553 A | 4/1996 | Segalowitz | 128/696 |
| 5,513,645 A | 5/1996 | Jacobson et al. | 128/710 |
| 5,518,001 A | 5/1996 | Snell | 128/697 |
| 5,575,803 A | 11/1996 | Cooper et al. | 606/151 |
| 5,711,304 A | 1/1998 | Dower | 128/696 |
| 5,843,127 A | 12/1998 | Li | 606/232 |
| 5,846,198 A | * 12/1998 | Killmann | 600/424 |
| 5,879,297 A | * 3/1999 | Haynor et al. | 600/407 |
| 5,987,352 A | 11/1999 | Klein et al. | 600/509 |
| 6,038,469 A | 3/2000 | Karlsson et al. | 600/512 |
| 6,305,381 B1 | * 10/2001 | Weijand et al. | 128/899 |
| 6,308,093 B1 | * 10/2001 | Armoundas et al. | 600/509 |

\* cited by examiner

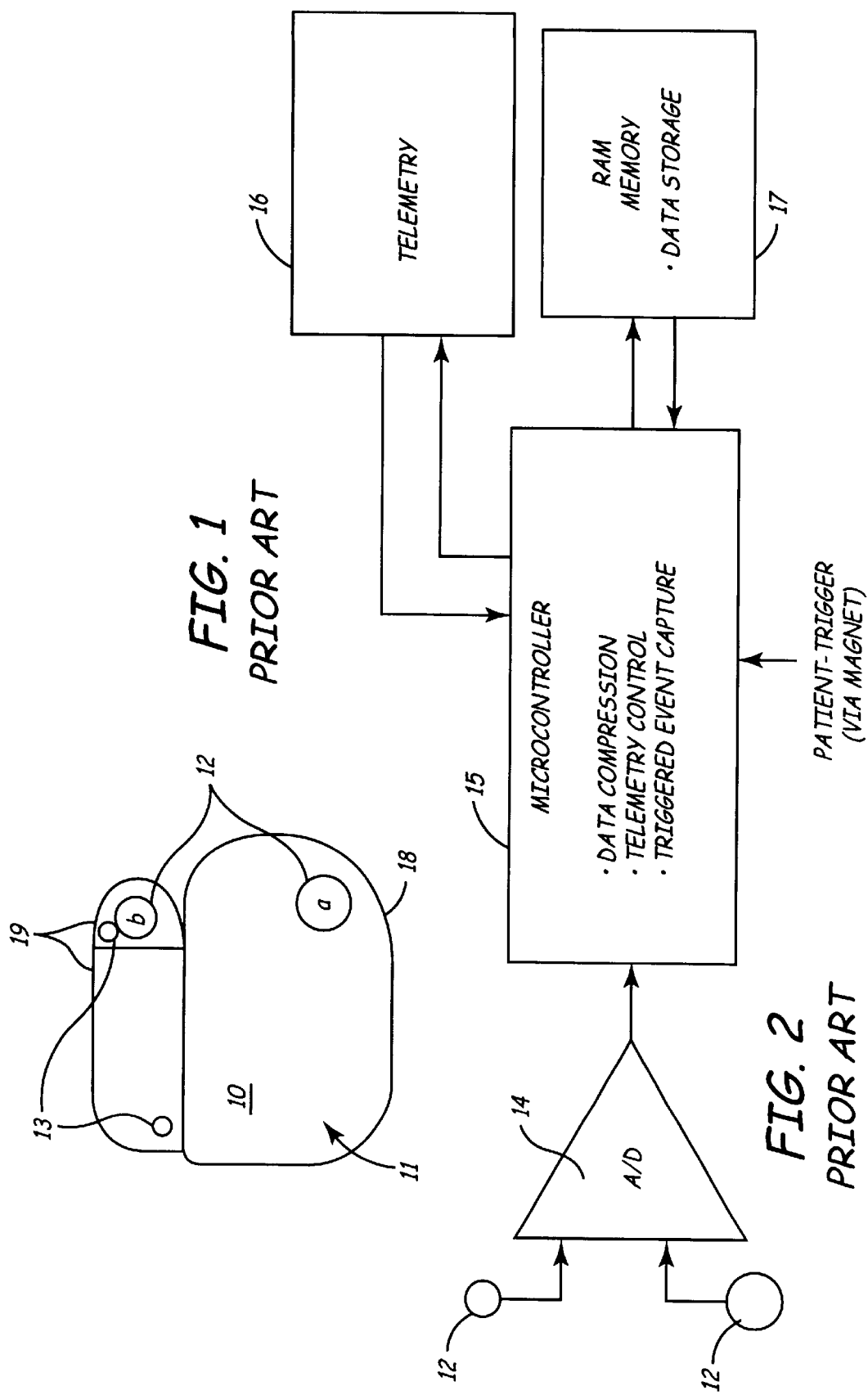

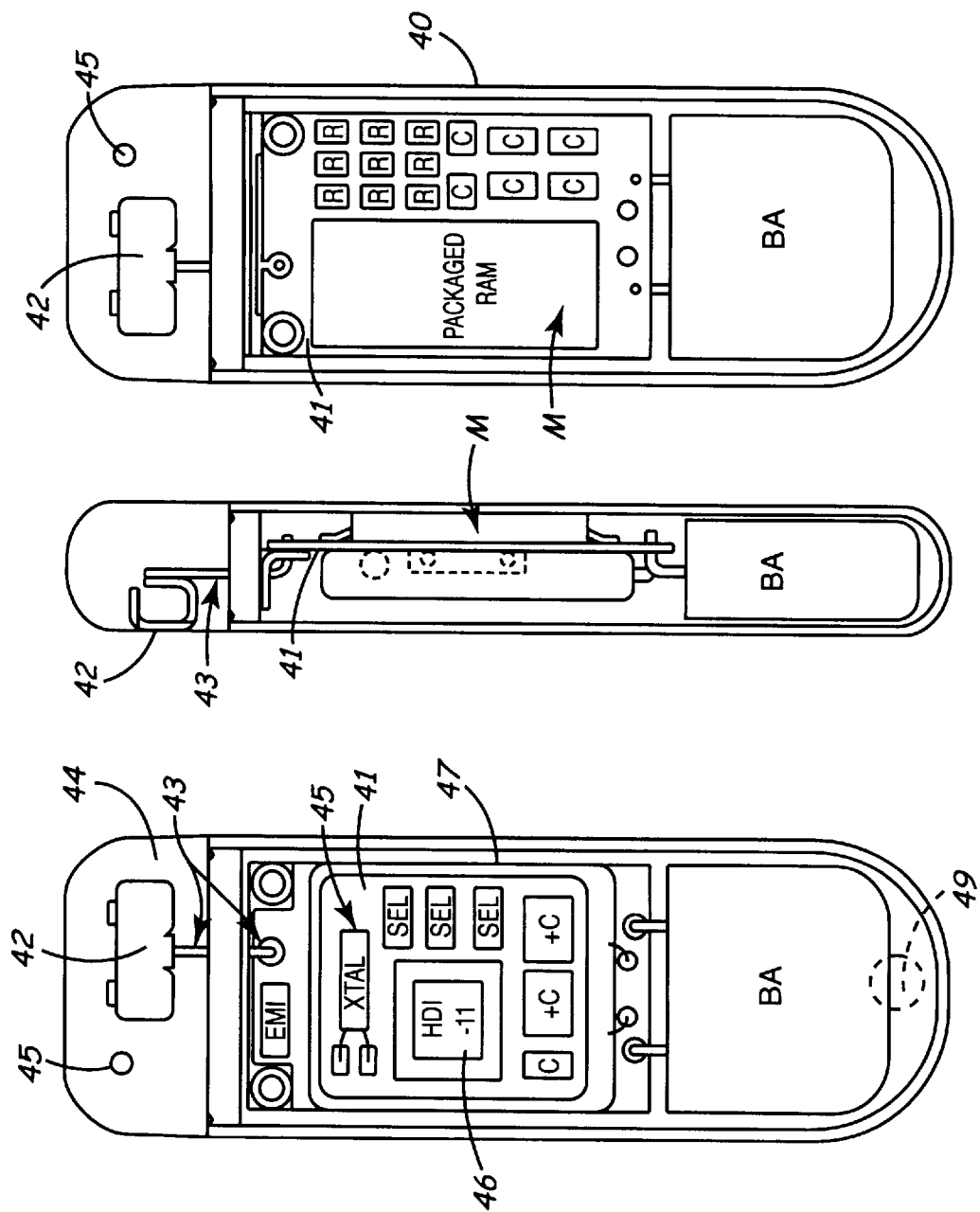

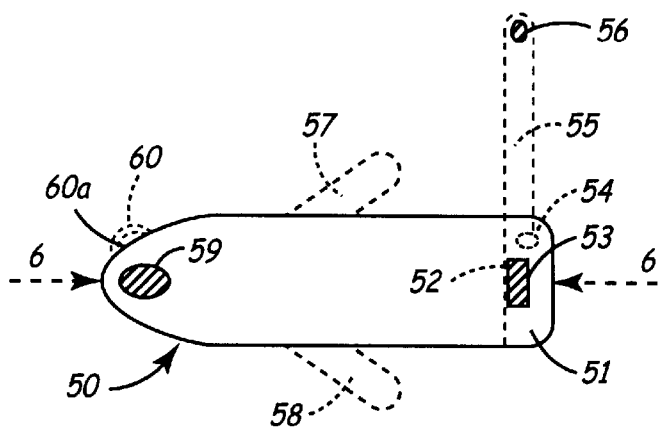
FIG. 5
FIG. 6A   FIG. 6B
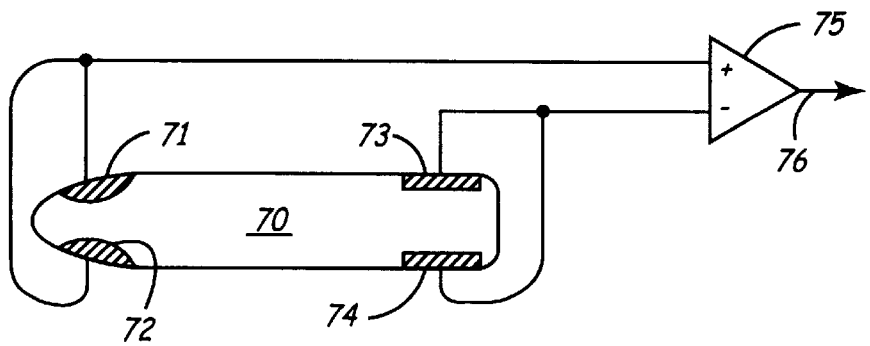
FIG. 7A
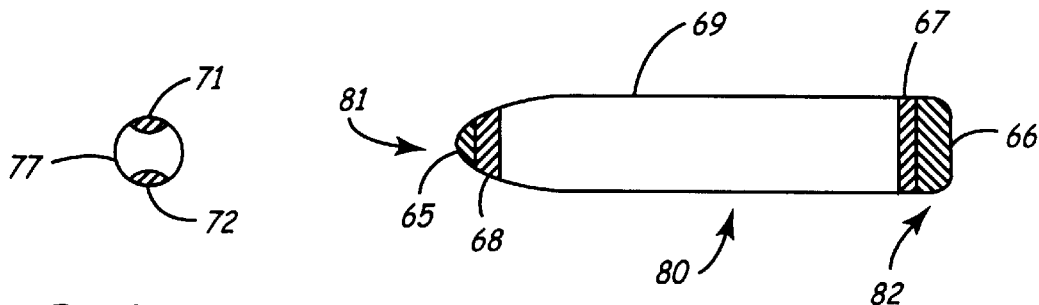
FIG. 7B
FIG. 8

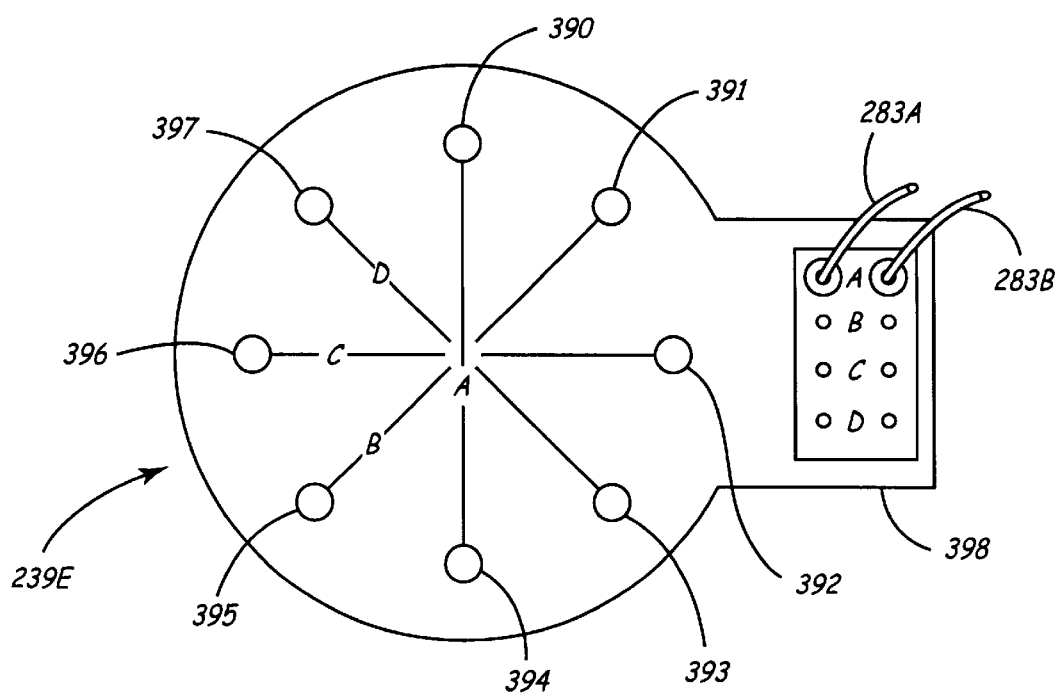
FIG. 19
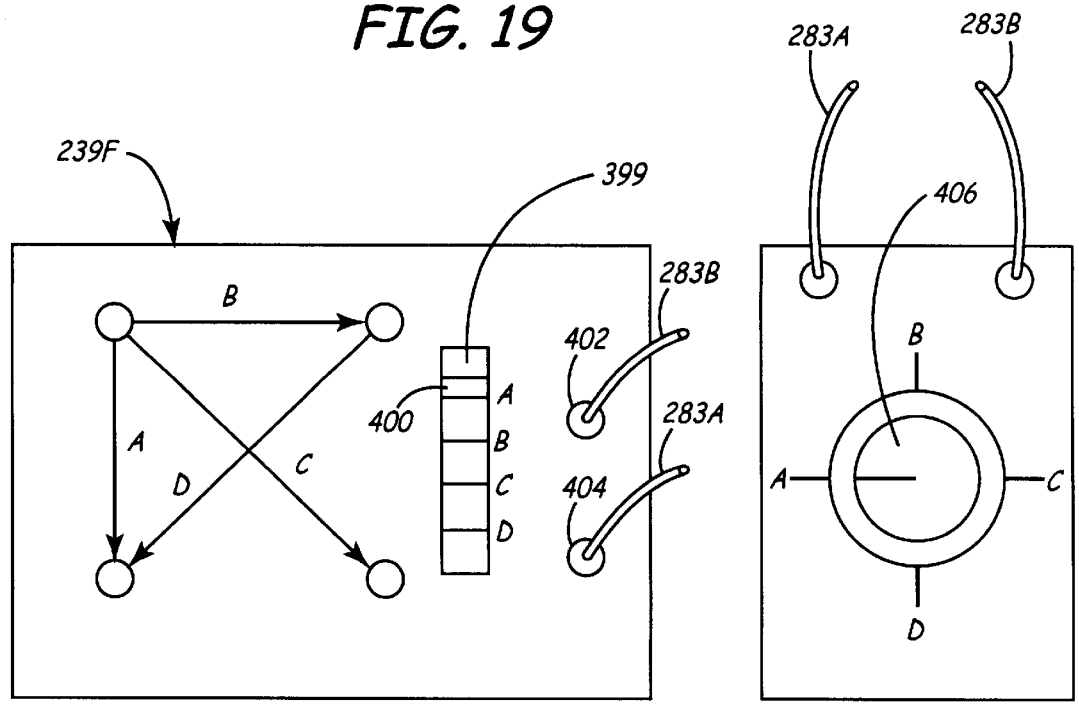
FIG. 20
FIG. 21

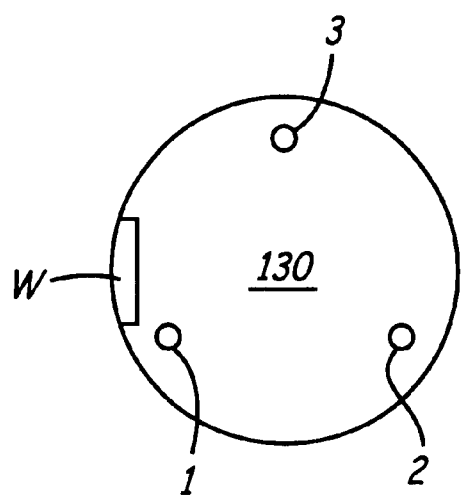 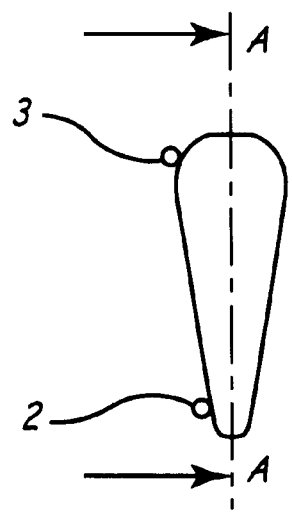
FIG. 24A  FIG. 24B
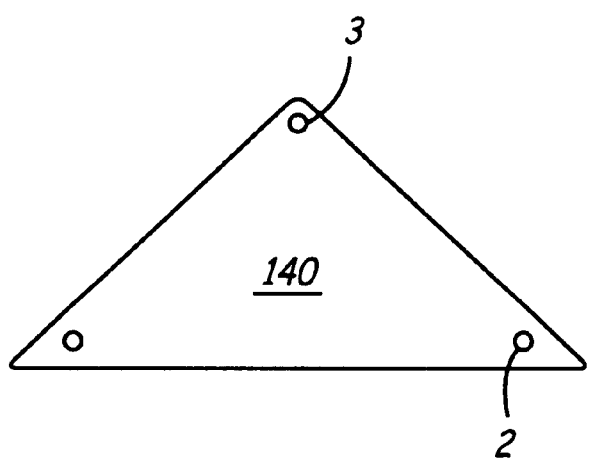 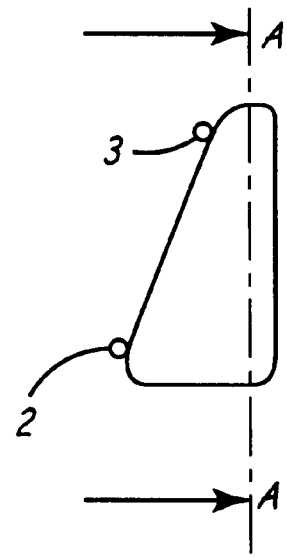
FIG. 25A  FIG. 25B

SYSTEM AND METHOD FOR NON-INVASIVE DETERMINATION OF OPTIMAL ORIENTATION OF AN IMPLANTABLE SENSING DEVICE

CROSS-REFERENCE TO CO-PENDING APPLICATIONS

This application is a continuation-in-part of U.S. patent application Ser. No. 09/384,176 filed Aug. 27, 1999 entitled "Tool for Insertion of Implantable Monitoring Device and Method", now U.S. Pat. No. 6,142,490, which is a division of U.S. patent application Ser. No. 09/033,678 filed Mar. 3, 1998, which issued as U.S. Pat. No. 5,987,352 on Nov. 16, 1999, which is a continuation-in-part of U.S. patent application Ser. No. 08/678,219 filed Jul. 11, 1996 now abandoned.

This application is related to, and includes common subject matter with, co-pending U.S. Patent Application entitled "System and Method for Deriving a Virtual ECG Signal", filed on even date herewith, and which is incorporated herein by reference in its entirety.

FIELD OF THE INVENTION

This invention relates to a system and method for non-invasively determining the optimal orientation for implanting a device for sensing physiologic events.

BACKGROUND OF THE INVENTION

Syncopal events and arrhythmias of the heart are particularly problematic for diagnostic physicians to observe in living patients. These events, can be of short duration and sudden onset, coming with little or no warning, and may happen very infrequently. Holter monitors are well known for monitoring electrocardiograms periods of time amounting to days or perhaps a week, but these are bulky and interfere with the patient's normal life, making them impractical for long term use. Further, patient compliance cannot always be guaranteed, and is a common problem in use of the Holter devices. Problems with external monitors and associated recorders also include inability of some patients to abide the attendant skin irritation. Bulky or expensive special purpose devices may need to be available and maintained. Removal is required for showering, and so on. Any time a living body needs to have a long term monitoring of a physiologic event that is intermittent or infrequent or both, all these problems come into focus. Therefore, there exists a need for minimally intrusive long-term monitoring of the patient's physiologic events and status. This is particularly indicated in, but not limited to patients with cardiac arrhythmias and vasovagal syncope to provide sufficient evidence for diagnostic purposes and for research into the causes and effects of such events. Patients have come to accept long term implants of small items for many things, including birth control, for example, like the "Norplant" (™ of Wyeth Laboratories) devices which secrete birth control hormones for perhaps a year before they need replacing. Accordingly it is believed that small device implants for long term implant will be well tolerated by the patient population.

Many attempts to address some of these problems have been made and met with limited success. The problem has been long existing. The Instromedics approach is seen in the Mills, et al patents (U.S. Pat. Nos. 5,333,616; 5,289,824 and 5,111,396) for a wrist worn monitor for ECG's which include features like patient triggering and microprocessor determination of event types (QRS detection). Wrist worn devices are also shown in the Righter patents issued to assignee Ralin, including U.S. Pat. Nos. 5,226,425 and 5,365,935. Jacobsen, et al in U.S. Pat. No. 5,513,645 describes multiple resolution storage for ECG's (ELA Medical is the assignee), and Snell's U.S. Pat. No. 5,518,001 vaguely describes a patient triggered recording device with multiple sensors and patient triggering(assigned to Pacesetter). InControl's approach is seen in the Yomatov patents, U.S. Pat. Nos. 5,411,031 and 5,313, 953 which seems to concentrate on beat to beat timing records, suggests the use of an arrhythmia detector, and does mention the possibility of leadless electrodes for monitoring cardiac signals. Examples of an external monitor/recorders can be found in Segalowitz' patents, including U.S. Pat. No. 5,511, 553, and Salo's U.S. Pat. No. 5,417,717. Another well known event recorder is the "King of Hearts" (™ of Instramedix) which records pre-event and post-event data.

Monitoring can be done using implantable pulse generators such as pacemakers and other heart stimulating devices or devices with leads in the heart for capturing physiologic parameters, including the ECG. However, the expense and risk from implanting a pacemaker or changing out one without these functions is something both patients and physicians would prefer to avoid. Such devices, in addition to performing therapeutic operations, may monitor and transmit cardiac electrical signals (e.g., intracardiac electrograms) to an external diagnostic devices typically with leads fixed in the patient's heart, to observe electrical activity of a heart. It is common for implanted cardiac stimulation devices to send intracardiac electrogram signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

For example, U.S. Pat. No. 4,223,678, entitled "Arrhythmia Recorder for Use with an Implantable Defibrillator", issued to Langer et al. on Sep. 23, 1980, discloses an arrhythmia record/playback component within an implantable defibrillator. ECG data is converted from analog to digital (A/D) form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry. Langer et al. in U.S. Pat. No. 4,407,288, entitled "Implantable Heart Stimulator and Stimulation Method", issued Oct. 4, 1983, discloses a programmable, microprocessor based implantable defibrillator which senses and loads ECG data into a memory via a direct memory access operation. A processor analyzes this ECG data in the memory to detect the occurrence of an arrhythmia event afflicting a patient's heart. Upon such an event, the defibrillator may generate a therapy to terminate the arrhythmia event and store the ECG data sequence of the event, for transmission to an external monitoring device and later study. In normal circumstances, when no arrhythmia event is occurring, the defibrillator continuously overwrites the ECG data in the memory.

U.S. Pat. No. 4,556,063, entitled "Telemetry System for a Medical Device", granted to D. L. Thompson et al, 1985, teaches a pulse interval telemetry system capable of transmitting analog data, such as sensed intracardiac electrogram signals, without converting analog data to a digital numeric value. The Thompson et al. telemetry system is capable of sequentially transmitting both digital and analog data, individually and serially, in either an analog or a digital format, to a remote receiver. The features and capabilities of these pacemaker/defibrillator devices is now well known, but the problems in long term monitoring for events and adequate recordation remain.

In the December 1992 Vol. 15 edition of PACE (15:588), a feasibility study was done for implantable arrhythmia monitors and reported in an article by Leitch et al. Subcutaneous, Bipolar "Pseudo-ECG" Recordings using an Implantable Monitoring System and at chaired poster presentation of the North American Society of Pacing and Electrophysiology (NASPE) an implantable monitoring system was described using the pacemaker that had been altered to use a point on the can as an electrode and to have an electrode mounted into the connector block thereof. This was presented to NASPE in Munich in 1994 by Brian Lee of Medtronic, Inc. A photograph of the device shown in that poster presentation was published by the American Heart Association Inc. in 1995 by Andrew Krahn, M.D. in an article entitled "The Etiology of Syncope in Patients with Negative Tilt Table and Electrophysiological Testing", pp. 1820 of CIRCULATION, 1995; 1992. The initial thinking for this started in NASPE 1991 in an Abstract published in PACE, 1991, 14:677 authored and titled: Leitch, J W, Klein, G J, Yee, Lee BB, Kallok, M, Combs, B, Bennett, T: Feasibility of an Implantable arrhythmia Monitor.

Further, a leadless implantable sensor for cardiac emergency warning was described in U.S. Pat. No. 5,404,887 issued to Knowlan et al. which detects heart events through impedance measurement sensed using a coil. See also Yomato et al, U.S. Pat. No. 5,313,953 which describes (in FIG. 26) a large but leadless implant.

With sufficient hardware and connections to the body, numerous other physiologic parameters may be sensed as is pointed out in U.S. Pat. No. 5,464,434 issued to Alt and U.S. Pat. No. 5,464,431 issued to Adams et al.

Although important benefits are provided by leadless implantable sensing systems, these systems also present some unique challenges as well. In particular, signal-to-noise ratios are often inferior as compared to devices that employ sensors positioned on leads implanted within the patient. To ensure that signal quality is maintained, it is important to properly position the implantable sensing device within the patient. However, because the physiology of each patient differs, the optimal device position and orientation will also vary from patient to patient. Therefore, some system is needed to ensure that optimal positioning of the implantable device is obtained on a patient-by-patient basis.

BRIEF DESCRIPTION OF THE DRAWINGS

FIGS. 1 and 2 are the exterior side view, interior block diagram, respectively of a prior art implantable device.

FIGS. 4a, 4b, and 4c are exposed front, side, and back views, respectively of a preferred embodiment of a substantially leadless implantable device.

FIG. 5 is an illustration of another embodiment of a substantially leadless implantable device, showing locations for fin/wing and stubby lead features.

FIGS. 6a and 6b are front and side views of preferred embodiment cross-sections taken from FIG. 5.

FIGS. 7A, and 7B are front, and cross section views of another embodiment of a substantially leadless implantable device.

FIG. 8 is a front view of yet another embodiment of a substantially leadless implantable device.

FIG. 19 is an implementation of the electrode patch having electrodes arranged in a circular configuration.

FIG. 20 is a diagram illustrating an electrode patch 239F that utilizes a sliding switch.

FIG. 21 is a diagram illustrating an alternative selection mechanism including a dial switch.

FIGS. 24a, 24b, 25a and 25b are front and side views of alternate embodiments of the invention.

SUMMARY OF THE INVENTION

Figure 3:
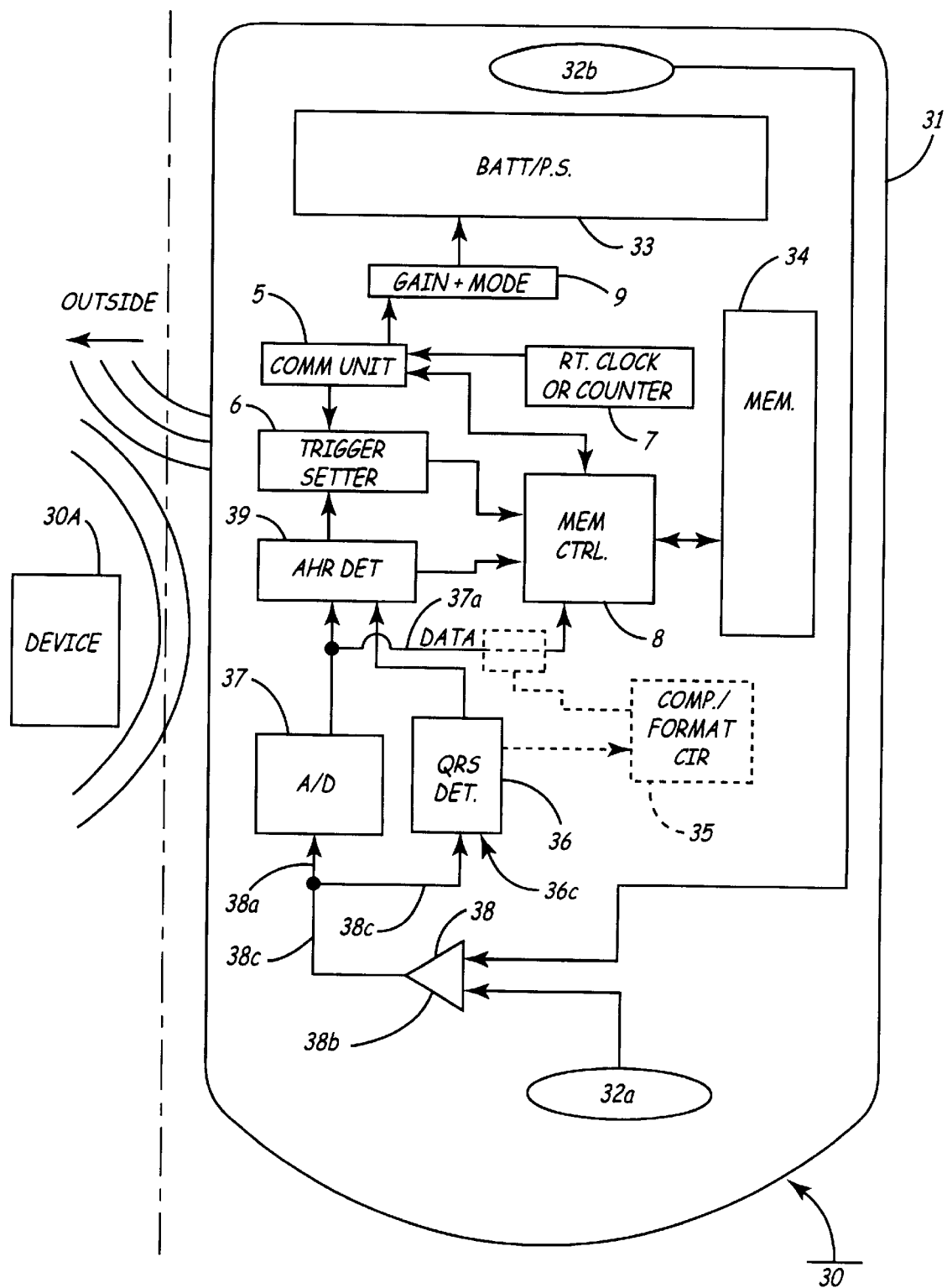
FIG. 3 is a block diagram illustrating the main circuit and assembly of a substantially leadless implantable device in accord with a preferred embodiment.

A system and method is disclosed for determining the optimal positioning of an implantable system within a body. The invention is particularly useful for determining the orientation of a device that uses a leadless electrode system to perform sensing. According to a most simple form of the invention, electrodes are positioned on an external surface of a body, and an ECG monitoring device is used to measure cardiac signals between various pairs of the electrodes. One or more of the electrodes may be re-positioned until an electrode pair position and orientation is located that provides a maximum signal reading. This position and orientation may then be used as the position and orientation in which to implant a corresponding device. In the preferred embodiment, the electrode size and spacing used to determine implant positioning approximate the electrode size and spacing of the implantable device.

In one embodiment, the ECG monitoring device used to measure physiologic signals is a handheld device having electrodes coupled to one surface of the device. Measurements are taken between various electrode pairs by placing the surface containing the electrodes in contact with the surface of the body. This device may further include a mechanism to allow a user to manually enable the measurement of physiologic signals between selectable electrode pairs. For example, the device may include jumper locations that are selectable by a user for connecting electrodes to a connector block to facilitate measurement of a signal between a selected electrode pair. In another embodiment, selected electrode pairs may be enabled automatically via an electronic switch and a processing circuit. The processing circuit may also be utilized to automatically determine the electrode pair providing the maximum signal amplitude. In one embodiment, the positioning of the electrodes on the surface of the monitoring device is adjustable. This allows measurements to be taken that correspond with the electrode spacing provided by various implantable devices.

According to another aspect of the invention, signal measurements A and B are taken between two electrode pairs. An optimal angle of implant may then be determined using vector arithmetic. If the two electrode pairs are orthogonally-related, the optimal angle is equivalent to the arc-tangent (B/A), wherein this angle is measured from the electrode pair that provided measurement A. This optimal angle of implant may be determined by the processing circuit, for example. Additional candidate angles of implant may be determined by repeating the processing using additional electrode pairs. A linear extrapolation process may be utilized to determine an optimal angle of placement at intermediate positions.

A second embodiment of the invention involves the use of an electrode patch having at least one electrode pair coupled to the patch. The electrode patch is positioned on the surface of the body, and is coupled to a device that measures physiologic signals between a selected pair of the electrodes. The patch may be re-positioned to obtain additional measurements between the electrode pairs provided by the patch. If multiple electrode pairs are coupled to the patch, measurements may be taken between the various electrode pairs by changing the position of jumpers that connect selected electrodes to a connector block. Alternatively, the patch may include multiple affixation devices for coupling to electrodes. This allows the electrodes to be positioned on the patch with a selectable spacing and orientation. In this embodiment, the electrodes may be disposable while the electrode patch is reusable. In one embodiment, at least one of the electrodes is slidably coupled to the patch to facilitate the adjustment of electrode spacing. Color-coded gel may be used with the electrodes to provide an indication on the body surface of the optimal position and orientation as determined by the inventive system and method.

DETAILED DESCRIPTION OF THE PREFERRED EMBODIMENT

A. System Background Information

In the past, implantable electrode sensing systems generally employed leads located in the heart to sense the cardiac signal. This is because subcutaneous electrodes located below a patient's skin have not been highly effective in producing good monitoring devices, and have not found commercial medical success. A well-known example of a system having leads which also contained more than a single electrical contact in the body of the pacemaker was described in U.S. Pat. No. 5,331,966 issued to Bennett et al. in 1994. The data recording system described in this invention requires only two electrode surfaces.

A prior art implantable sensing system is described with reference to FIG. 1 and appeared at a NASPE (North American Society of Pacing and Electrophysiology) conference as a poster presentation in 1994. The device 10 was provided with two suture holes 13 and two spaced apart non-lead or leadless electrodes 12 at one and one-quarter inches distance center to center. The device was coated with paralene indicated by arrow 11 so that the only area of exposure on the body of the pacer can 19 is the exposed area at the electrode 12a. The other electrode is a metal plug electrode 12b mounted in a connector block 19.

In FIG. 2 the same electrodes 12 supplied signals into the circuitry inside the housing or "can" 18 (FIG. 1) by first entering an analog to digital conversion and amplifier circuit 14. Data from this circuit 14 was fed to a microcontroller 15 which provided functions of data compression, telemetry control and event capture triggered by patient operation. Telemetry block 16 and RAM memory storage 17 were also provided in this device. The device described in the Yamato et al patent, (U.S. Pat. No. 5,313,953, FIG. 26) is quite complex and in any case, built for deeper implant than is this invention in its preferred uses.

Practical Considerations in Adopting Preferred Structure Design

A small and easy-to-implant, primarily leadless device, or one having a very short lead-like structure, device will require a minimal incision size, which is good for the patient. This can vary if the physician wants to use sutures to hold the device in place or for other reasons as needed. Between ½ and 1 inch incisions are preferred to avoid trauma and scarring. If significant concern exists regarding scarring, both ends can be tapered.

For ease of insertion the device should be easy to self-position, and preferably elongate in shape to maximize signal strength for a given volume by having electrodes spaced at far ends of the length or longitudinal axis of the device. The larger the device the more electronics and larger the battery volume can be. Both the functionality provided by extra electronic circuits and battery volume may be traded for enhanced useful life and minimal complexity when considering the optimum device size. Although it is preferred that the electrodes be widely spaced on opposite ends of an elongate device, variations to this theme may be acceptable for alternative monitoring missions. The primary mission of the preferred implant is long term ECG event monitoring.

Refer now to FIG. 3 in which a circuit model 30 is illustrated in an outline of an implantable device shell 31. Electrodes 32a and 32b bring signal from the body to an input mechanism 38, here drawn as a differential amplifier for simplicity only, the output of which is fed to a QRS detector 36 and an A/D converter 37. Both these circuits 36 and 37 supply output to an arrhythmia detector 39, which in this preferred embodiment supplies the autotrigger signal to the trigger setting circuit 6. The data output from the analog to digital converter may be converted, compressed, formatted and marked or reformulated if desired in a circuit 35 before the data is ready for input into the memory 34. The memory control circuits 8 receives input from the A/D converter, with or without conversion and so forth from circuit 35, from the auto triggering determination circuit (here seen as the arrhythmia detection circuit) 39 (which may include input directly from the QRS detector if desired) as well as signals from the trigger setter circuit 6. The trigger setter circuit may also be controlled by a communications unit 5 which operates to receive and decode signals from the outside of the implant 30 that are telemetered or otherwise communicated in by a user. This communications unit 5 will also be able to communicate with the memory controller to request the offloading of memory data for analysis by an outside device. It should contain an antenna a or other transceiver device or circuitry to communicate with an outside device such as device 30A. A clock or counter circuit 7 reports the time since start or real time to the outside interrogator device 30A contemporaneously with a data offloading session so that the events recorded in memory 34 may be temporally pinpointed.

Alternatives to this overall design may be considered, for example by using a microprocessor to accomplish some or all of the functions of circuits 6, 8, 39, and 35 but it is believed that such a design will not provide the power and size savings taught by use of the preferred design.

FIGS. 4*a–c* illustrate one preferred form 4 of a substantially leadless implantable sensing device. In this form it has an outer titanium shell 40, in a plastic cap means 44, which together form the exterior of the device. The cap means 44 may be composed of material similar to those used for pacemaker connector blocks as it is in the case. The two electrodes, 44 and 49, provide metal surface contacts to the body. Electrode 49 is formed as a whole in a paralene coating over the metal body 40, of the device. The metal electrode 42 is connected via a feedthrough 43 which is itself electrically connected to the circuit board 41. Circuit board 41 contains all the electronics required for the device function and is connected to a battery BA for power. An integrated circuit 46 houses circuitry and intelligence required for the function and the memory M is packaged on the other side of the circuit board. In this preferred form, the invention uses a communications circuit 45 having a telemetry antenna both to indicate from outside the body that a read out is requested of the device, and for communicating data out from said device. Programming of the device or mode setting will also use the communications circuit 45. In this form also a suture hole 45 is provided through the cap means 44. Electrode 49 is connected by a conductive connection (not shown in this fig.) to the circuit board. In this embodiment the length "1" is 2⅜" and "w" is ¾". These measurements can be varied within the constraints described. Electrode spacing here is about 1¾", center to center.

FIGS. 5 through 8 are diagrams of alternative embodiments of an implantable sensing device having three or more electrodes. A third electrode, like electrode 56, can be used to optimize signal strength responsive to changes in device position, heart position, or body position. A transistor or other switch means can switch the electrode configuration automatically based on a determination of signal strength or direction from an outside device through the communications circuit. In order to retain the elongated shape yet provide a well spaced orthogonal position, the third electrode can be mounted on a self-positioning (flexible, rigid, or semi-rigid) stubby lead. An additional variation from the most preferred design could provide for a wing or fin-shaped member 57 or more than one wing (57, 56) that extend substantially in one plane from the main body of the device. Ideally this would be approximately in the same plane as the other two electrodes(53 and 59). Unless they are constructed so as to spring from the main body outward after insertion into the intended body area, wings like 57 or 58 will require a larger incision than the currently most preferred device, a smooth bodied device. The illustration of the device 50 in FIG. 5 without the dotted line external parts 55, 57, 58, and 60, would be such a most preferred form.

Some other features are also significant and should be noted. A single suture hole 54 (or two or more if desired) can be provided in the cap. Additional suture appendages, like ring 60, having a suture hole 60a, may additionally be provided for more stability. Additionally, a suture may secure the stubby lead to the patient's tissue if desired. These suture holding means allow the device to be fixedly held in one orientation in the body of the user, whether intramuscular or strictly subcutaneous. Intramuscular pocket implantation is advantageous in that the device may be protected from the outside world by a layer of muscle, which will provide cosmetic benefits to the patient as well. The exact sites of implant may advantageously be varied from patient to patient for various reasons apparent to the physician. Implant just under the skin now appears to provide a signal most free of skeletal muscle myopotential or body movement signal interference.

Another important feature of the shape is to have one end of the elongated device tapered to aid in easily inserting under the skin during implant/insertion (as in a blunt dissection procedure). This self-placing tapered tip helps ensure that the device stays positioned properly in alignment with the principal cardiac vectors whether they be the principal R-wave, or P-wave vector or best for both, especially where two sutures would be used at the cap end. It is believed that this taper feature will be better than just a blunt placement with an instrument. Another preferred method of implant could be injection of the tapered end into the body, using a device similar to that described in the U.S. Pat. No. 5,520,660, the Implant Plunger. As a secondary feature the other end from the insertion tip may be blunt or otherwise formed to assist in providing a better directing and pushing surface during insertion.

Figure 26:
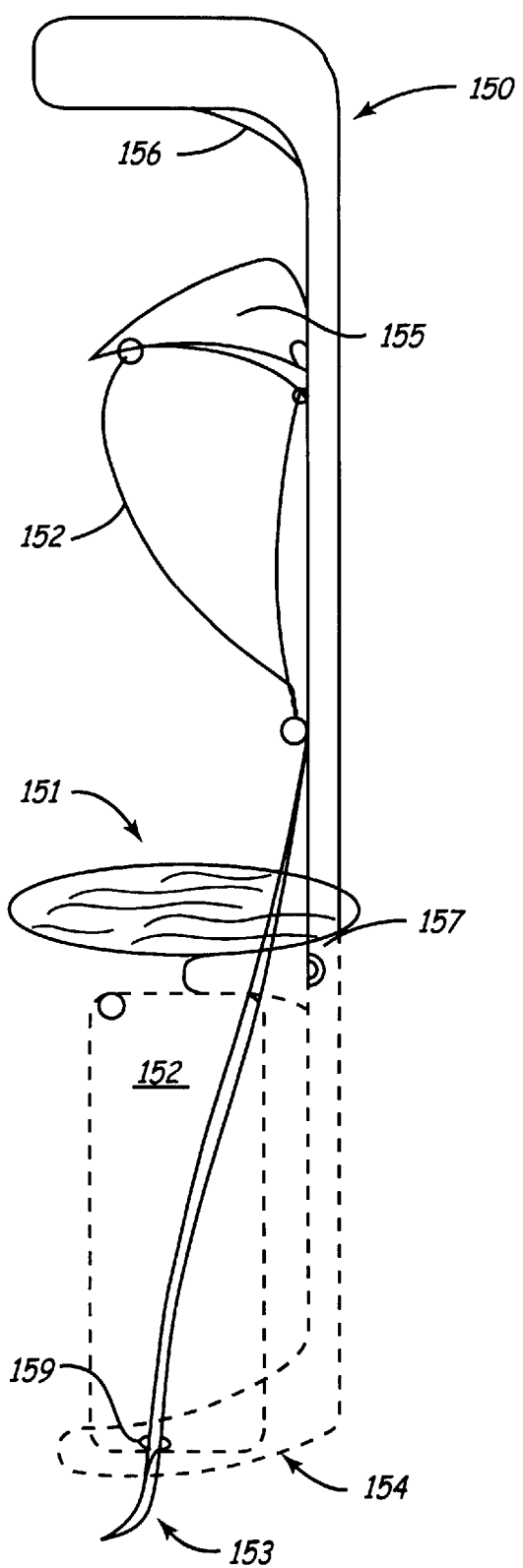
FIG. 26 is a diagram of an insertion tool for implanting the device in accord with this invention.

FIG. 26 is a diagram of an alternate tool having a handle unit with a blade 154 for making an insertion into the opening 151 created in the skin, and for holding the implant 152 between a recess behind the blade and a pushing member 157 until a handle releases the pushing member. The handle 155 may advantageously tie the end of a suture into the patient beneath the skin with tool 153, which is then retrieved by manipulation of a wire 157, thus accomplishing insertion and securing the implant at the far end 159, rather than at the cap end of the implant. Many variations on this injection and insertion theme can be accommodated within the teachings of this document.

These kinds of instrument-assisted insertion are herein referred to generally as insertion via a "trocar" concept. In general this "trocar" concept involves any instrument which encloses the implantable device and contacts the surface of the body or point of incision, starts the incision and allows the device to be inserted into the incision. The trocar is used to make a starting hole/incision using a sharp point and/or cutting edge first. The physician then uses the mechanical advantage provided by the trocar to stretch the incision wide enough to allow the implantable device to fit through the incision and then pushes the device under the skin (or into the muscle, etc.) in one motion. The incision could be enlarged to facilitate suturing if desired.

A preferred form of insertion tool should be fitted with a smooth protective chamber (preferably plastic lined) just wider than the implantable device (but of approximately the same cross-section) to slip the implantable device into, tapered end toward the insertion end of the tool. The bottom of the chamber could be shaped to fit the taper of the implantable device and would move out of the way when the implantable device was pushed by hand or an injecting plunger. The outside of the bottom of the chamber would come to a sharp point and possibly have cutting edges tapered back on both sides from the sharp point, but may not need to cut to the full width, instead it could stretch the initial opening to allow insertion of the implantable device with a push.

Suturing to hold the implant device in place could be done automatically or with surgical staples by some means associated with the tool, the device could be left in the pocket, or it could be held in place by a coating of its surface with a sticky substance or one that adheres to body tissue like silicone rubber, or it could be inserted with a properly shaped Parsonnett pocket, although this would likely interfere with the gathering of signal through the electrodes.

While considering the features of the embodiments illustrated by FIG. 5, the electrode configuration may be noted. Electrode 53 is a conductive or metal plate compatible with the patient's body that is on one surface of the cap unit 51, the cap being delineated by dotted line 52. One can construct the device 50 as a solid container having out of body compatible materials. For examples, titanium or other metal or alloy, coated with compatible insulator but exposed for at electrode areas or fitted with conductive electrodes, ceramic having conductive areas thereon, etc. One should have two surface electrode areas separated by a distance (functionally similar, therefore, to electrodes 53 and 59 in FIG. 5) for the device to work. This distance should be at least far enough to achieve good signal but not too far so as to make the size of the implant too large to accommodate. In one preferred embodiment, electrode spacing is slightly greater than 1¾ inches, center to center. This distance can range between ½ and 2½ inches, or even near 4 inches before becoming impractical.

In the presently preferred embodiment, the cross-section is an easy-to-insert rounded rectangular or oval shape to the potential of the device turning over after implant. FIG. 6A shape 61 and FIG. 6B, shape 62 illustrate this concept. Any similarly functional cross-sections configurations may be used. Studies have determined that electrodes that are faced outward, toward the skin of the patient, are preferable to face in or other electrode orientations. This may be due to less muscle exposure or movement or other noise sources.

Additional features are illustrated which can assist in preventing medically unintended movement of the device. In FIG. 7A the electrodes are placed so as to be matched on opposite sides of the rectangular, round, or ovoid shaped device and electrically connected in parallel on opposite sides to retain the same signal in spite of flipping or other movement. (The internal circuitry would operate like the op-amp 75 to produce output 76 from electrodes 71–74 as shown to produce this effect.) In surface pacemaker implants, patient populations have been known to play with their implants, often unconsciously and this has been a common enough problem in the pacemaker art to have obtained the name "twiddler's syndrome." These features address this problem. The device of 7A is seen in cross-section in FIG. 7B.

FIG. 8 is a diagram of another embodiment of an implantable sensing device employing circumferential electrodes on a cylindrically shaped device. The illustrated device can be seen to also have a body 69 that is tapered on one end 81 and blunt on the other 82. The effect again is to provide a constant signal in spite of likely unwanted rotation of the device, because the electrodes each extend around the device circumference. Here the electrodes 65 and 68 are provided for end 81, and electrodes 66 and 67 are provided for end 82. This approach trades-off the protection from muscle noise of the rectangular outward-facing device.

FIGS. 24A and 25A illustrate yet other alternative embodiments of an implantable device. These embodiments would be most feasible for designs employing a minimum amount of circuitry, and having reduced power requirements. Corresponding side views are provided by FIGS. 24B and 25B. These devices have three electrodes each shown as electrodes 1, 2, and 3, to adjust orientation to the best signal if desired. However two electrode forms and forms with windows W for sensors are also contemplated.

Description of the Invention

As can be appreciated by the foregoing background information, many advantages exist in employing a monitoring device that has an electrode system that is substantially leadless. However, the use of leadless electrodes also presents unique problems, as discussed above. To ensure that a leadless electrode system can be used in a manner that maximizes signal quality, it is very beneficial to determine optimal positioning and orientation of the device prior to implant. This is particularly necessary since the physiology of each patient differs, and thus the optimal positioning of a device within a body will vary from patient to patient.

One mechanism for determining optimal orientation prior to implant involves employing an external ECG measurement device using external electrodes. Many different types of external electrodes are well known in the field of cardiology. By observing the ECG at orthogonal electrode orientations in roughly the positions preferred by the physician/patient, the signal amplitudes of P-wave, R-wave, and T-wave can be monitored until a good positioning is found and the signals are of an optimal amplitude. These measurements may be made while the patient is positioned in several typical postures to account for posture variability, if desired.

The electrodes should be spaced at approximately the same distance as exists between the electrodes of the implantable device, within a factor of two or so. Additionally, electrodes of approximately the same diameter as those of the implantable device should be used. It should be noted that the diameter of the external electrodes in most ECG systems will be smaller than the edge to edge spacing of the electrodes by greater than roughly a factor of two or so. Several systems are disclosed below that determine the optimal position and orientation of an implantable device having substantially leadless electrodes.

Embodiment 1

Standard ECG Electrodes

Figure 9:
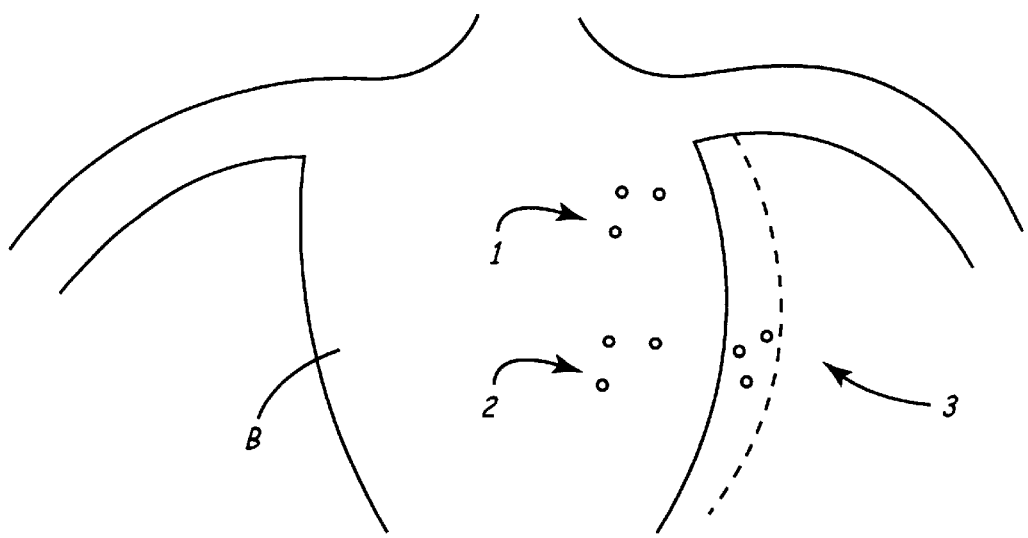
FIG. 9 is a drawing of a patient body segment with specific locations referenced thereon.

In the most simple form of the invention, a standard ECG Monitoring System can be used with the standard electrodes and electrode preparation of the skin. The electrodes are placed in orthogonal patterns of the proper electrode spacing over each candidate implant site as described in the above paragraph per FIG. 9.

Orthogonal measurements are taken over each candidate implant site, illustrated as locations 1, 2, and 3, on a patient's body. Two or more electrodes are used to take the measures. The current example illustrates the use of three electrodes being used in an orthogonal pattern.

According to one method of the current invention, signal amplitudes may be noted using the orthogonally-positioned electrodes. It may be assumed a similar implant orientation will result in a similar signal reception. Movement of the electrodes may be performed until a satisfactory signal reading is obtained at a given location and orientation.

For a more exact orientation to produce the absolutely best and largest R-wave, vector arithmetic may be used in the following manner:

If the two orthogonally-oriented electrode pairs with a common electrode produce R-wave Amplitudes A and B, the optimal orientation will be at the angle=Arc–Tangent(B/A), where this angle is taken from the common electrode to the electrode producing R-wave amplitude A. The same procedure can be followed for optimizing the P-wave and T-wave amplitude. One can also use similar calculations to determine the best compromise angle for P, R, and T waves.

This standard ECG approach has the advantage of being possible using commonly found ECG monitoring systems, but has the disadvantage of requiring surface preparation of the skin, as well as requiring repositioning of electrodes if the "best" orientation is desired.

Embodiment 2
Hand-Held Device with Fixed Electrode Probes

Figures 10A, 10B:
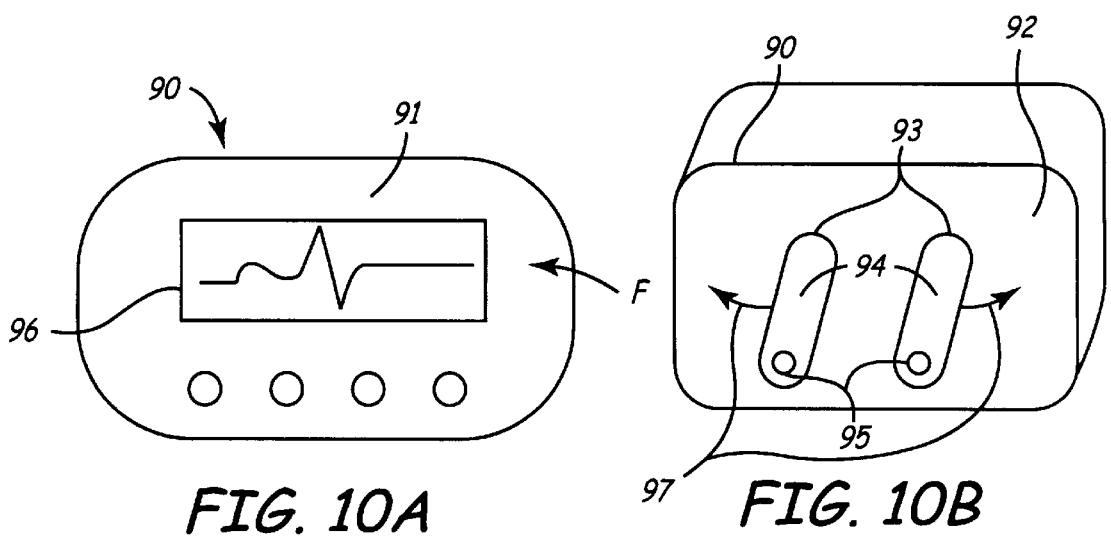
FIGS. 10A and 10B are front and back views of a testing ECG device for use with this invention.

FIG. 10A is a diagram of a handheld device uses to determine optimal orientation of an implantable device. This device 90, which is similar to a hand-held emergency heart monitor provided by several manufacturers, can be used to probe the surface locations and orthogonal orientations that are desired in order to find the optimum orientation. Signal measurements may be performed with two or more electrodes residing on at least one surface of the device in a manner to be discussed below. This device will be customized with electrode size and spacing that matches a particular associated implantable device. This is necessary to provide accurate measurements. The device of FIG. 10A may display the ECG on an attached recording device or display, or on a built-in display such as an LCD monitor. The exemplary embodiment includes a customized hand-held portable ECG monitor of the type commercially available from the Micromedical Industries Inc. of Northbrook Ill., such as the Paceview™ system.

FIG. 10B is a back view of the system of FIG. 10A. In this embodiment, a raised electrode assembly constructed on points 93 supports posts 94 and electrodes 95, and maintains the proper test position of the electrodes for the device being considered for implantation. In this embodiment, these additional structures may be adjusted to have a spacing similar to that of the implantable device as shown by arrows 97. This allows placement and orientation data to be accurately calculated for a selected implantable device.

Figure 11:
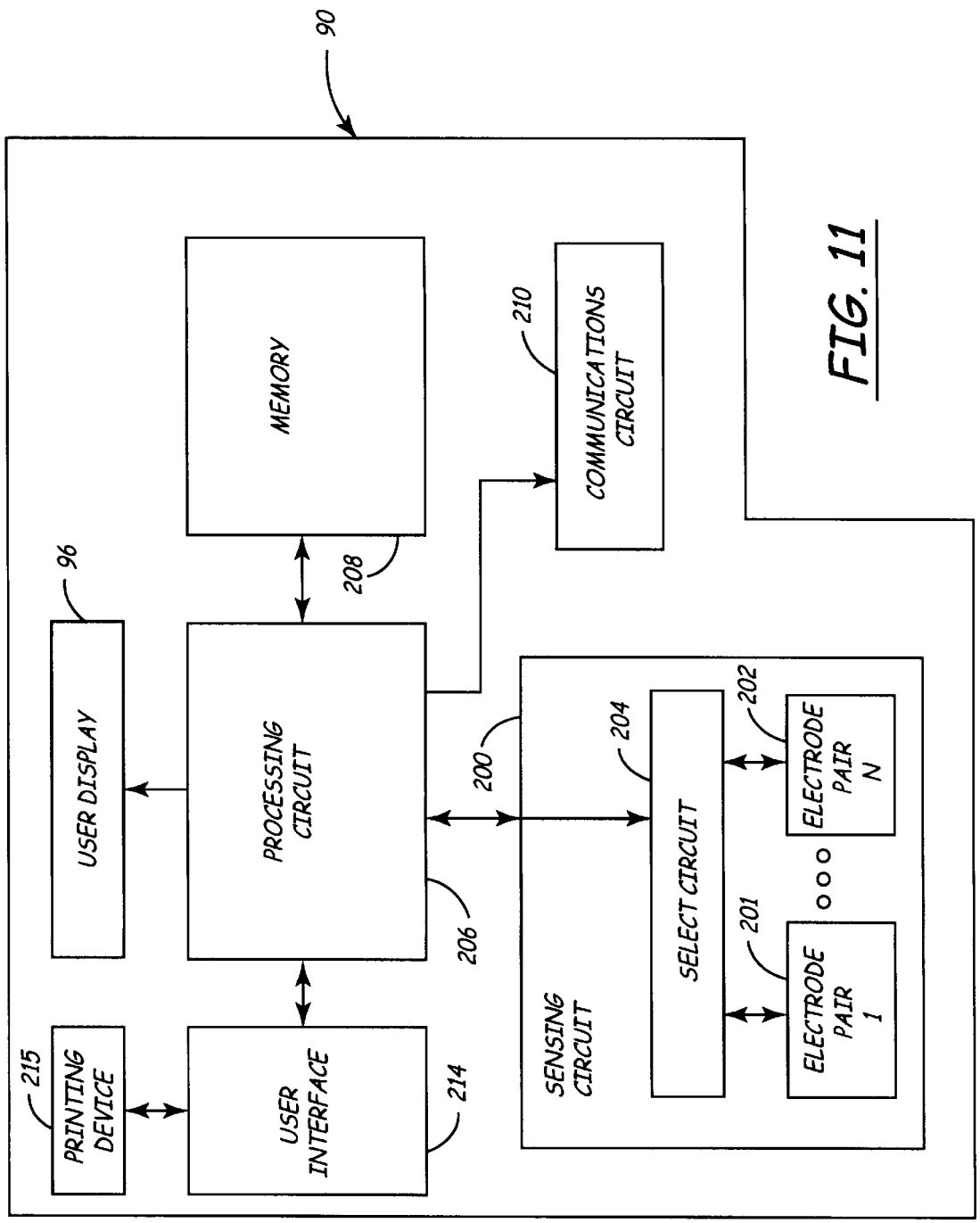
FIG. 11 is a system block diagram of various components that may be included within the hand-held device shown in FIGS. 10A and 10B.

FIG. 11 is a system block diagram of various components that may be included within the hand-held device 90 shown in FIG. 10A. A given embodiment may include one or more of the components shown in FIG. 11. The device of FIG. 11 includes a sensing circuit 200 having multiple electrode pairs 1 through N shown in blocks 201 and 202, respectively. These electrode pairs may be coupled to a select circuit 204 that is selectively enabled by processing circuit 206. By enabling various electrode pairs, multiple signal measurements may be taken sequentially. Alternatively, if a higher-performance system is desired, one or more measurements between electrode pairs could be provided to the processing circuit 206 in parallel. In this case, the processing circuit may include multiple interfaces, each to receive the multiple measurements in parallel. Additionally, if a parallel design is employed, it may be possible to eliminate select circuit 204.

Measurements various ones of the electrode pairs may be stored in a memory 208 for later retrieval, if desired. Alternatively, these measurements could be immediately transferred via a communication circuit 210 to an external system such as a programmer. Communication circuit 210 could be a telemetry antenna and related circuitry, for example. If desired, the measurements provided by the electrode pairs could be displayed along with orientation data on a user display 96 such as an LED display, for example. In another arrangement, processing circuit 206 could automatically determine the measurement having the largest amplitude, and utilize this measurement to determine optimal orientation of the implantable device.

A user interface 214 may be provided to allow user input to be received by the processing circuit 206. A user may push a button included in user interface 214 to signal the processing circuit that the hand-held device is in a desired candidate location and a measurement should be recorded, for example. Additionally, user interface could include some type of printing device 215 to provide a hard-copy of measurement results.

In one embodiment, processing circuit 206 may use measurements provided by electrode pairs that are orthogonally-positioned with respect to each other to calculate the optimal angle of positioning a device. This could be done using the method described above wherein an optimal angle is calculated as the Arc–Tangent of the ratio of two signal readings. This method is illustrated further below in reference to FIG. 12.

It will be understood that many alternative embodiments exist for the system shown in FIG. 11. For example, no memory 208 and communications circuit 210 may be needed if all readings are displayed on user display 96. Alternatively, no user display is needed if all information is transferred immediately to an external device via communications circuit 210. If desired, only a single electrode pair need be provided, with the user re-positioning the device to obtain readings for additional electrode orientations. In a most simple model, processing circuit is not needed, and measurements may be provided directly from an electrode pair to a display.

Figure 12A:
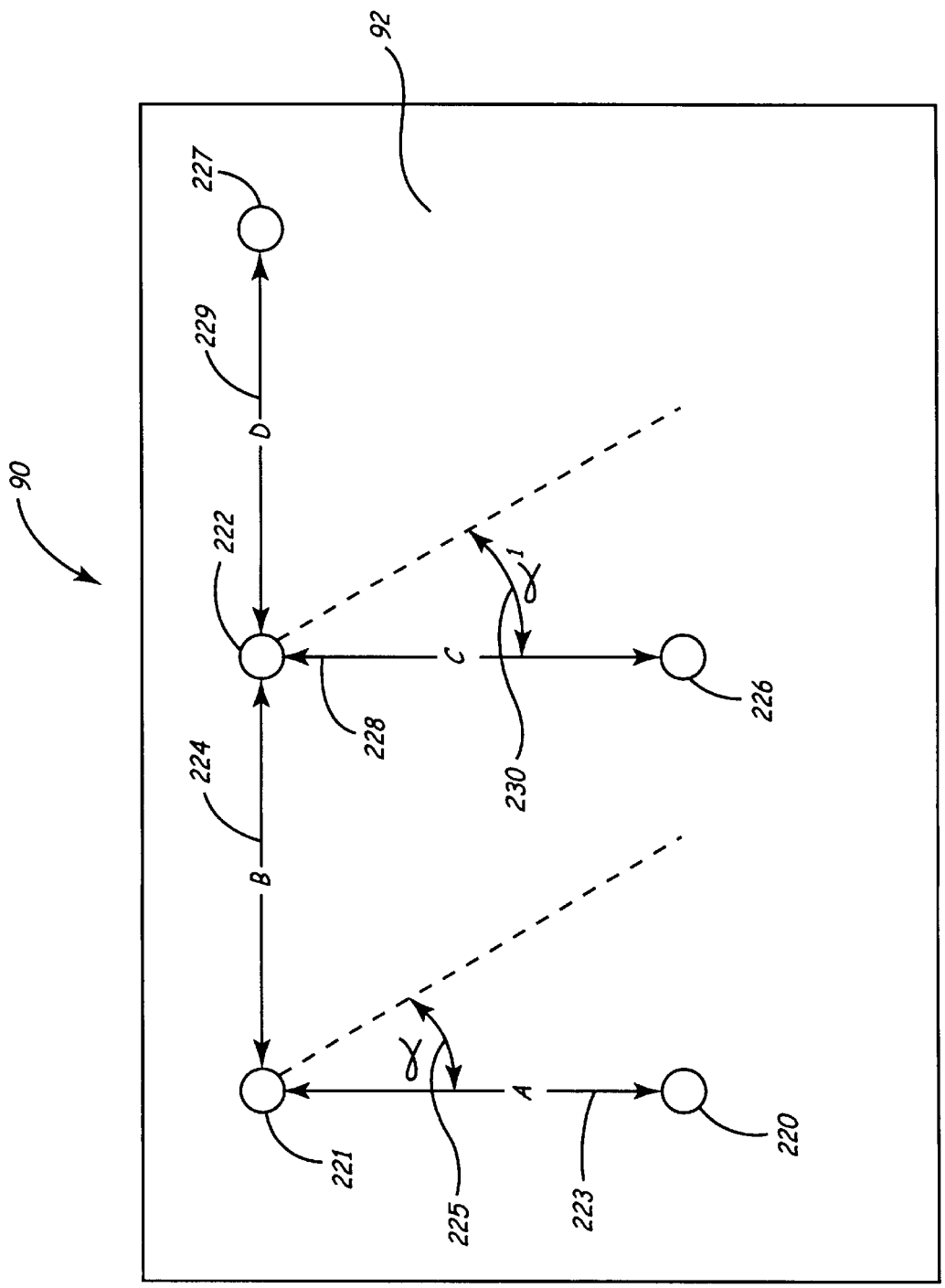
FIG. 12A is a diagram illustrating an alternative electrode configuration for the hand-held device shown in FIG. 10B.

FIG. 12A is a circuit block diagram of an alternative embodiment of the electrode configuration of the hand-held device, as shown in FIG. 10B. In this embodiment, three electrodes 220, 221, and 222 are positioned so that cardiac vectors A 223 and B 224 are orthogonal in orientation with respect to each other. Surface 92 is positioned such that these electrodes contact the patient's skin. Signal amplitude A 223 may be obtained between electrode pair 220 and 221, and signal amplitude B 224 may be measured between electrode pair 220 and 222. Using the method discussed below, a processing circuit such as processing circuit 206 may be used to calculate the optimal angle of placement α225 using the calculation $$\alpha = \text{Arc–Tangent}(B/A).$$

In an alternative embodiment, optimal angles of placement may be obtained with an electrode array. For example, additional electrodes 226 and 227 may be included. Additional measurements C 228 and D 229 may be taken to calculate a second potential angle of placement α'=Arc–Tangent(D/C). The angle α'230 is the optimal angle for a device placed within the region defined substantially by the triangle created by electrodes 226, 222, and 227, whereas the angle α is the optimal angle for a device placed within the region defined substantially by the triangle created by electrodes 220, 221, and 222. Although these two angles will be similar, they may not be exactly the same. If device placement is to occur somewhere between electrode 221 and 222, a linear extrapolation process may be used to determine the optimal placement angle. For example, for a device placed in the region substantially half-way between vectors A and C, an optimal placement angle substantially half-way between the angles α and α' may be used. It may be noted that the optimal placement position may be determined by finding the location where the ratio of the two signal measurements is at the maximum.

Figure 12B:
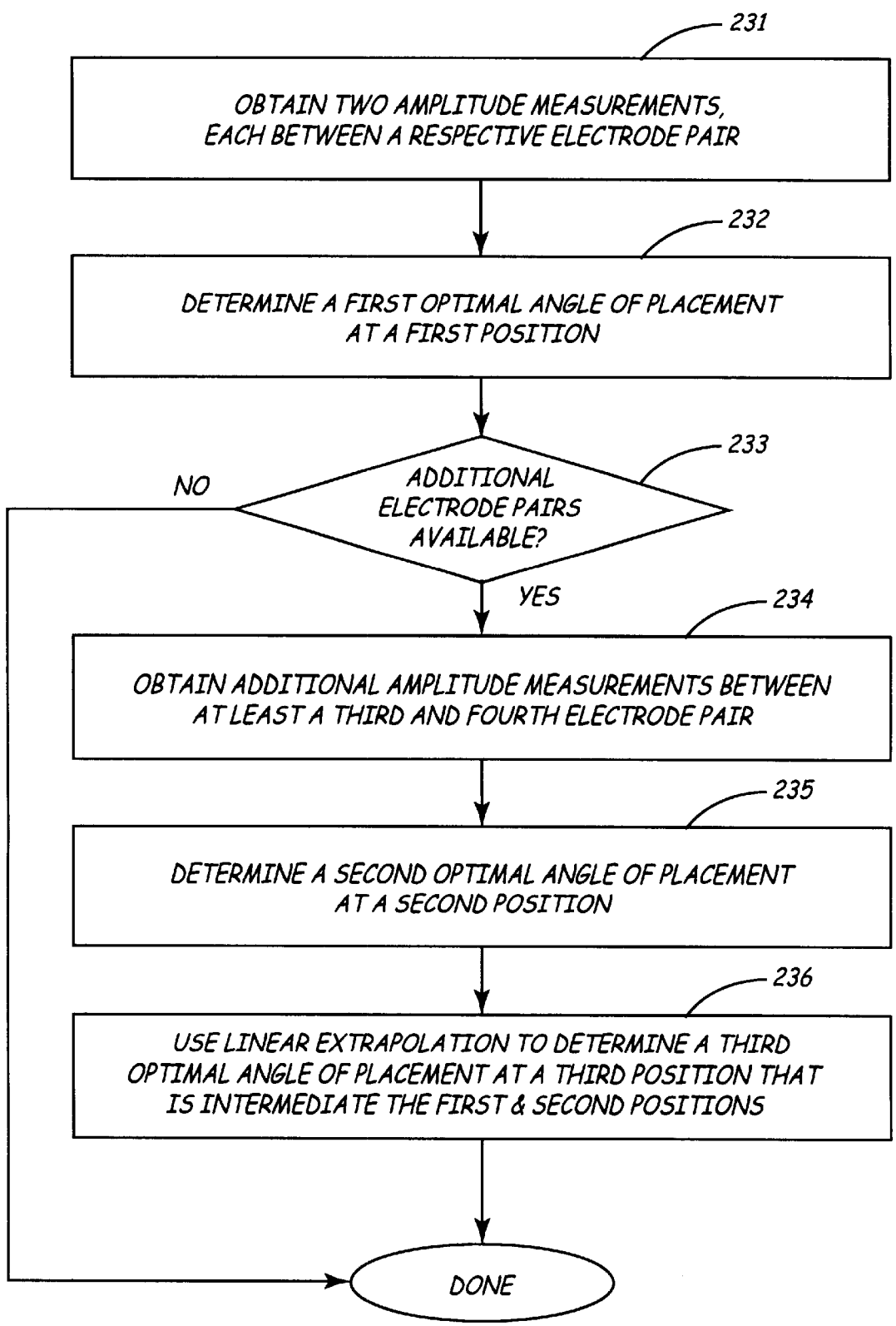
FIG. 12B is a flowchart illustrating one process that may be used to determine an optimal angle of placement of an implantable device as discussed in reference to FIG. 12A.

FIG. 12B is a flowchart illustrating one process that may be used to determine an optimal angle of placement of an implantable device as discussed in FIG. 12A. In step 231, two amplitude measurements are obtained, such as measurements A 223 and B 224 of FIG. 12A. In step 232, a first optimal angle of placement is calculated using the amplitude measurements. If more than three electrodes are available, additional amplitude measurements may be taken, as shown in steps 233 and 234, respectively. A second optimal angle of placement may be determined at a second position, as illustrated in steps 235. If device placement is to occur at some intermediate position between the first and second positions, a linear extrapolation process may be used to determine a third optimum angle of placement at the third position. This is shown in step 236.

Device 90 has many advantages as compared to the first embodiment discussed above. For example, placement of surface electrodes over the implant site is not required. Additionally, efficient measurements may be taken between multiple electrode pairs. As discussed above, a processing circuit may be used to automatically generate an optimal angle of placement. No wiring or external equipment is required, and the ECG can be seen in real time in monitor window 96.

Embodiment 3
Electrode Patch

Figure 13:
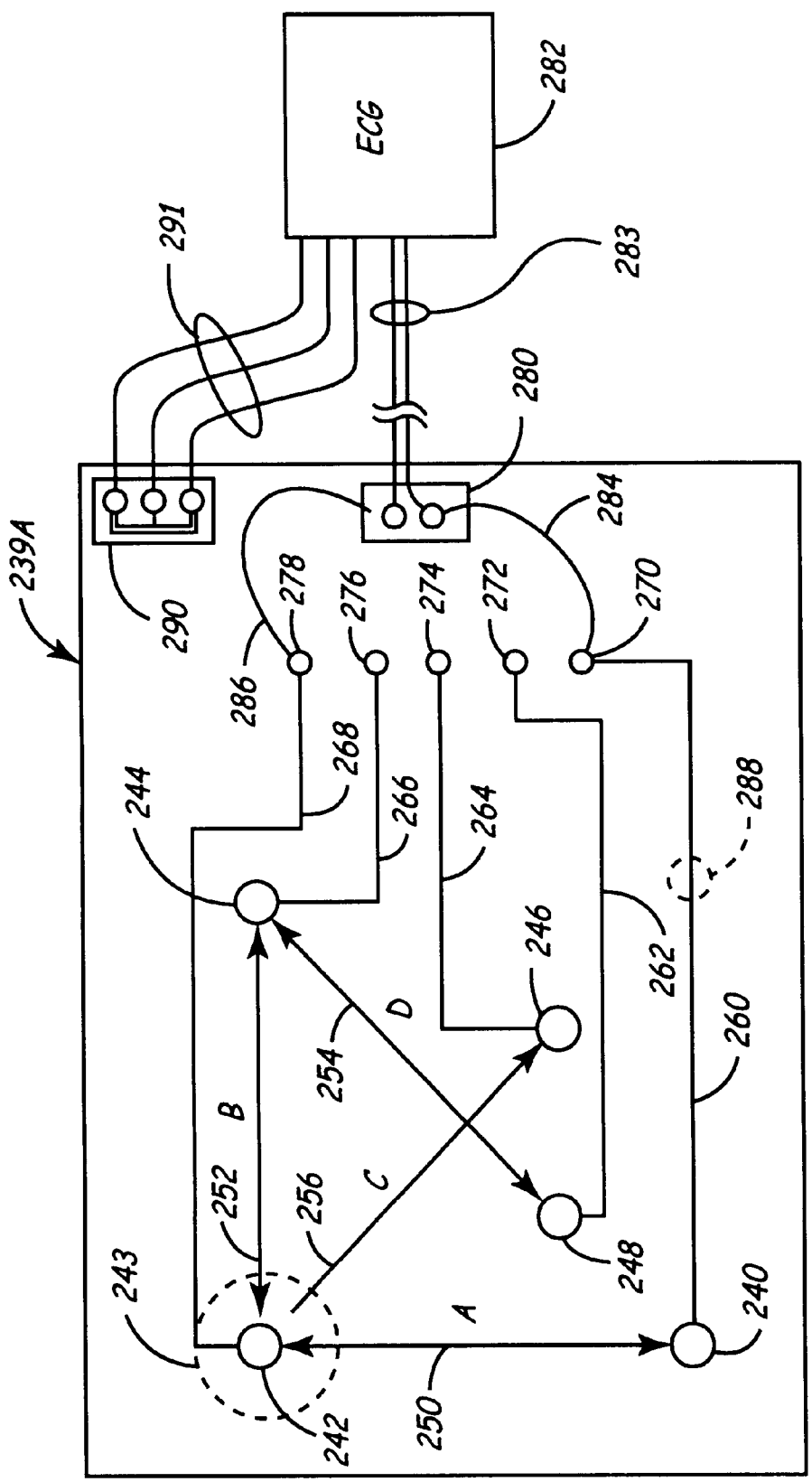
FIG. 13 is a diagram of an embodiment of the current invention that includes an electrode patch.

FIG. 13 is a diagram of an embodiment of the current invention that includes an electrode patch 239A. This embodiment includes a thin, flexible patch of the type that is commercially available for use with surface electrodes used when taking ECG measurements. Such patches may be made of many types of plastic, for example. Multiple electrodes 240 through 248 are coupled to the patch. Each electrode is provided with a central conductor, and a larger surrounding conductive surface area 243 (shown dashed) for contacting a patient's skin. Although this surface area 243 is shown only for electrode 242, it is understood that such a surface area is provided for all other electrodes 240 through 248.

In one embodiment, the electrodes are positioned so that various electrode pairs are spaced at substantially the same distance. For example, the current embodiment includes the electrode pairs indicated by arrows 250, 252, 254, and 256. The distance between the electrodes in each of these pairs is substantially the same, and is preferably matched to the electrode spacing of an implanted device.

The patch includes a mechanism for allowing readings to be selectively taken between various electrode pairs. In one embodiment, the electrodes are coupled via conductive traces shown as traces 260 through 268 to connectors 270 through 278, respectively. Two of the connectors 270 through 278 may then be selectively jumpered to a connector block 280. This connector block may be a standard connector block of the type used with an ECG monitoring device 282. Such a connector block could include any type of standard connectors such as metal conventional button snap connectors, for example. FIG. 13 shows electrodes 240 and 242 being jumpered to connector block 280 via jumpers 284 and 286, respectively, so that a signal amplitude between these two electrodes may be measured by an ECG monitoring device 282 when patch 239 is placed on a patient's skin. The ECG monitoring device may include the circuits shown in FIG. 11 to obtain measurements between various ones of the electrode pairs. For example, the ECG monitoring device may include a processing circuit that may be utilized to determine an optimal angle of placement according to the method illustrated in FIGS. 12A and 12B.

In another implementation, connector block 280 and all traces 260 through 268 may be eliminated. In this instance, the leads 283 from ECG monitoring device 282 may be connected directly to connectors on an opposite side of a selected electrode. This embodiment will be illustrated and discussed further below.

Using the electrode patch of the current embodiment, the jumper configurations may be changed by the user so that cardiac signal amplitudes may be measured between the various electrode pairs. The current embodiment allows measurements to be taken between two orthogonally-related electrode pairs 240/242, and 242/244, although it is not a requirement that these electrode pairs be positioned in an orthogonal relationship. It also provides measurements between electrode pairs 242/246 and 244/248 which may be positioned at approximately a 45° angle as compared to the orthogonally-positioned electrode pairs. If a more precise positioning is desired, the measurements taken between electrode pairs 240/242 and 242/244 could be used to generate a precise angle using the method discussed above in reference to FIG. 12. Patch 239A further includes a connector block 290 to receive the unused leads 291 of ECG 282. These leads include those that are typically provided to couple to the patient's extremities such as an ankle. These unused leads must be connected to connector block 290 so that the reference voltage of the ECG device 282 and the patch 239 are the same.

The current embodiment allows a fast, inexpensive, and easy way to quickly approximate the optimal position of a device that is to be implanted. If the jumpers 270 through 278 are provided on the opposite side of the patch as compared to the electrodes, the patch does not need to be removed from the patient's skin to take the successive readings between the electrode pairs.

In one embodiment, the electrode patches may be colored with one or more dyes to leave semi-permanent, colored reference marks on the patient's skin. For example, each electrode could be colored with a different dye included within the electrode gel. The reference marks are used to guide the surgeon in determining optimal position and orientation for the implant.

FIG. 13 shows an electrode patch in which distances between the electrode pairs is substantially equivalent. A more simple approach is provided by a four-electrode design that eliminates electrodes 248 and 262. This embodiment would include only electrodes 240, 242, and 244, with a fourth electrode being located at position 288 (shown dashed). In this case, the diagonal measurements are taken between electrodes 244 and 240, and between electrode 242 and the fourth electrode at position 288. Adjustments may be made in the measurements to account for the fact that the diagonal measurements are taken between electrodes spaced approximately forty percent farther than are the other electrode pairs. This adjust may be made using a linear scale factor, for example. Although this approach may be slightly less accurate, it eliminates problems that may occur by electrodes such as 240 and 248 shorting.

Figure 14:
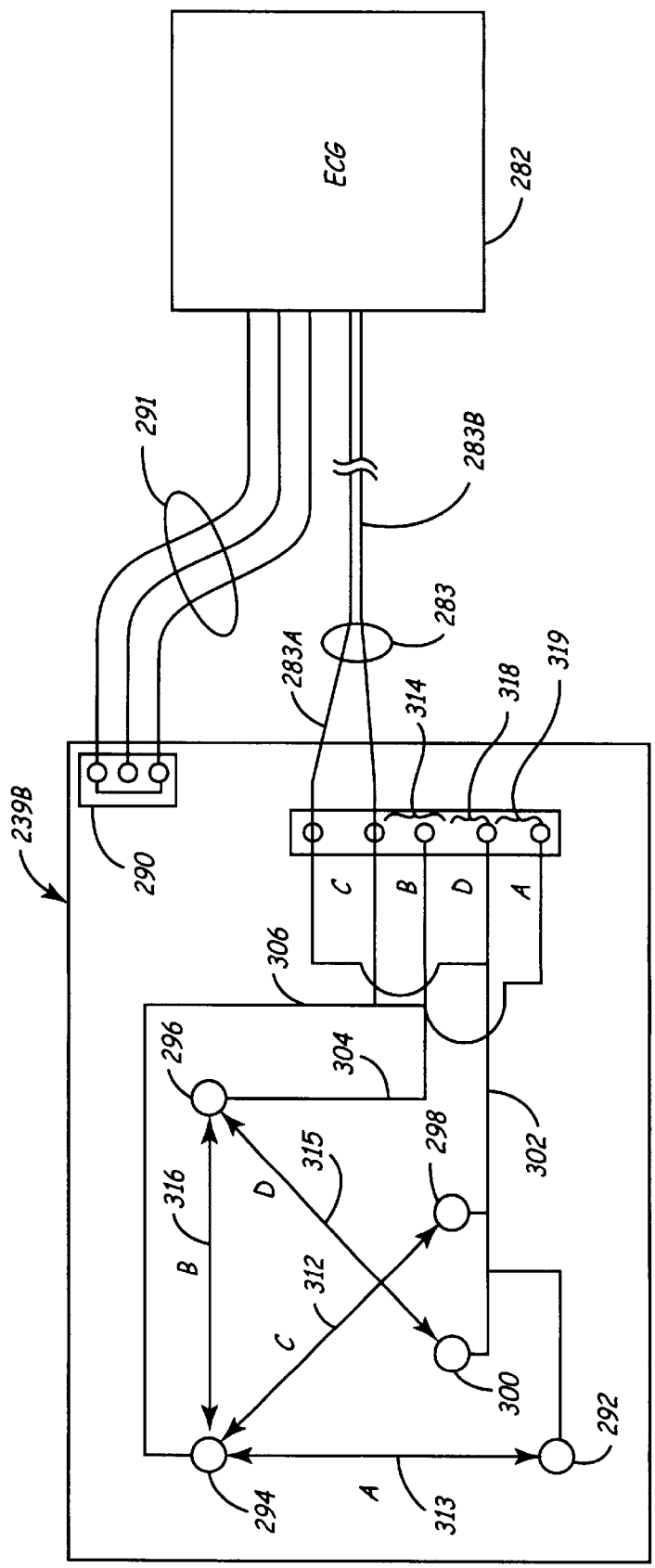
FIG. 14 is a diagram of an alternative embodiment of an electrode patch.

FIG. 14 is a diagram of an alternative embodiment of an electrode patch 239B. In this embodiment, affixation devices such as button snaps are provided at locations 292 through 300 to couple to an electrode. Each of the affixation devices are electrically conductive, and are coupled to a respective one of the conductive traces 302 through 306. Affixation devices 292, 298, and 300 share trace 302. Electrode pairs may be selectively affixed to ones of the affixation devices so that a desired reading may be taken by ECG measurement device 282. In this embodiment, a connector block 308 is shown that has three possible positions for receiving connector leads from the ECG device. When the ECG leads 283 are in the position shown, and electrodes are coupled to affixation devices 294 and 298, a signal having a directional vector corresponding to arrow C 312 is measured. Similarly, when the ECG leads 283 are in the position indicated by bracket 314 and electrodes are coupled to affixation devices 294 and 296, a signal having a directional vector corresponding to arrow B 316 is measured. ECG leads may be positioned as indicated by bracket 318 to measure a signal having a directional vector corresponding to arrow D 313 if electrodes are coupled to affixation devices 296 and 300. Finally, a signal having a directional vector corresponding to arrow A may be measured if electrodes are coupled to affixation devices 292 and 294 and the ECG leads are positioned as indicated by bracket 319.

In the embodiment of FIG. 14, only two electrodes are needed to accomplish measurements. In this embodiment, the electrodes are moved from one affixation device to the next to complete the various measurements. This movement of electrodes from one affixation device to the next requires the removal of the patch from the patient's skin between measurements, which may be inconvenient, and may degrade the effectiveness of any adhesive material provided on the electrode surface to facilitate skin contact.

Figure 15:
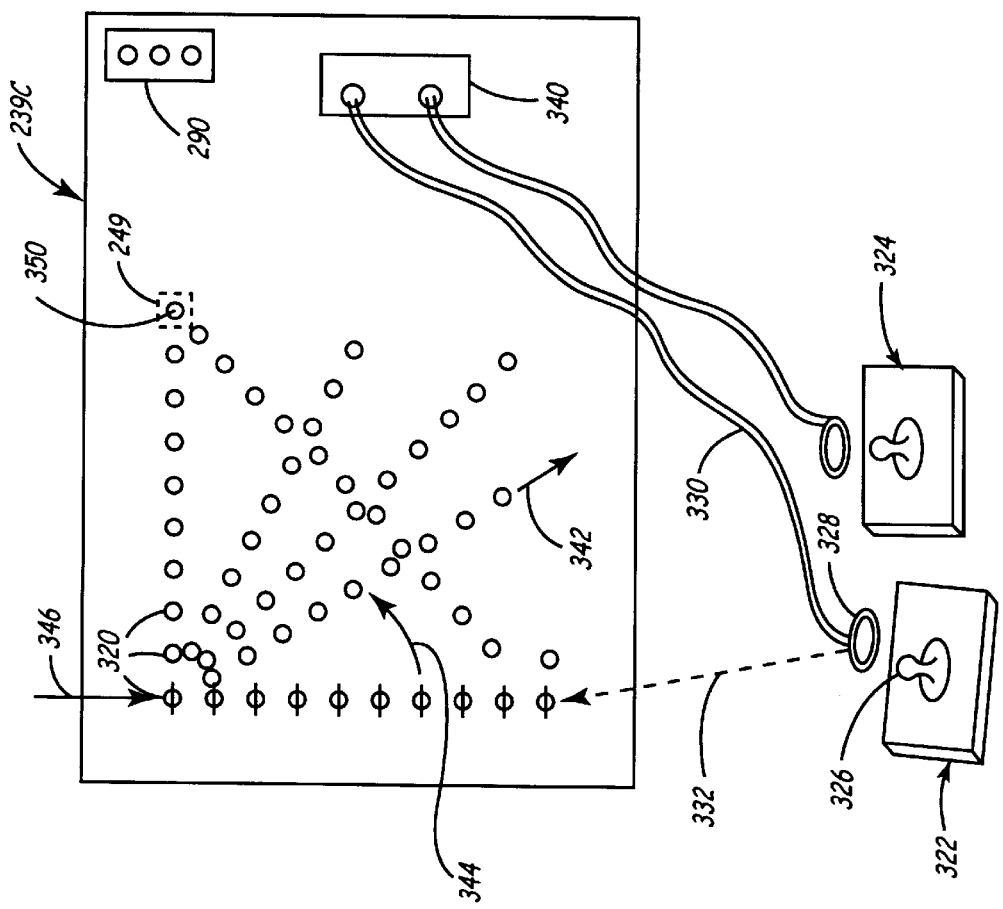
FIG. 15 is a diagram of yet another embodiment of an electrode patch.

FIG. 15 is a diagram of an alternative embodiment of an electrode patch 239C. In this embodiment, patch 239C includes apertures such as those shown as apertures 320. An electrode of the type shown as electrodes 322 and 324 may be used to couple to the patch 239C. Each of these electrodes includes an affixation device 326 such as a button snap that may be inserted through a selected hole and retained in place by a coupling device snapped onto affixation device 326 on the backside of the electrode patch 239C. Affixation device may be further adapted to couple to an electrically-conductive connector 328 at one end of a conductive lead 330. For example, the connector 328 may take the form of a collar that slips over affixation device to electrically couple to that device, and which is held in place between electrode patch 239C and electrode 322 when affixation device 326 is inserted into one of the holes of patch 239C.

On the opposite side of electrode 322 resides the electrode surface adapted to be placed on patient's skin for measuring ECG signals. A portion of this electrode surface is electrically coupled through affixation device 326 to connector 328, and further via lead 330 to connector block 340. The connector block 340 may be connected to an ECG device to measure ECG signals in the manner discussed above. When both electrodes are coupled to patch 239C in the foregoing manner and are placed on a patient's skin, ECG measurements may be taken to determine optimal orientation of a device that is to be implanted.

The embodiment of the electrode patch shown in FIG. 15 allows electrode spacing and electrode sizes to be varied based on the type of device that is to be implanted. As discussed above, the electrode size and spacing of the patch should approximate that of the implantable device. Moreover, this embodiment readily allows for the use of standard disposable electrodes, while the electrode patch 239C could be reusable.

It may be noted that more than two electrodes could be affixed to electrode patch 239C at once. For example, five electrodes could be affixed in a configuration similar to that shown in FIG. 14. In this configuration, a connector block and some sort of jumping mechanism similar to that shown in FIG. 14 is necessary.

It may be noted that a electrode patch 239C may include apertures that allow for the positioning of electrode pairs at any predetermined angle. For example, FIG. 15 shows a set of aligned apertures indicated by arrow 342 that could be used to measure a signal having a directional angle 344 from a base reference direction indicated by arrow 346. This higher resolution may be useful if the optimal orientation is to be more accurately determined.

The embodiment shown in FIG. 15 requires the use of connector block 340 and multiple leads 330. These structures may be eliminated by allowing the standard button snap connectors included on the ECG leads 283 to directly couple to an affixation device 326 of an electrode patch. The type of coupling mechanism that may be used in this instance is shown in FIG. 15 as may be affixed with a portion 249 (shown dashed) of electrode patch 239C.

Figure 16:
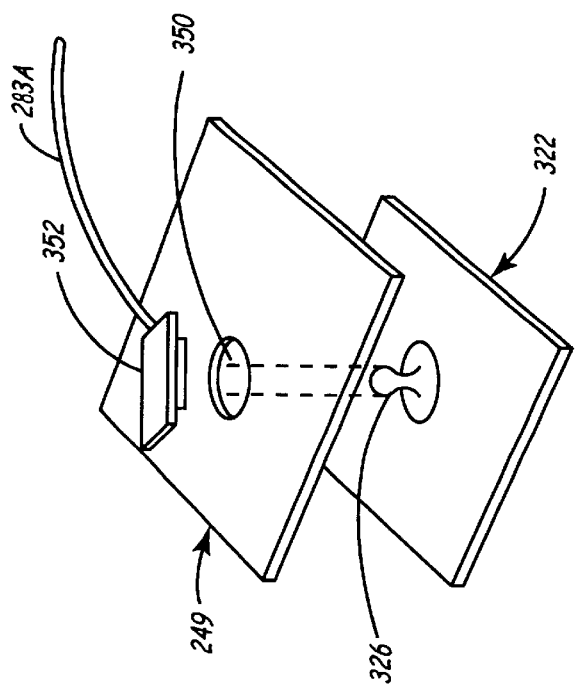
FIG. 16 is a diagram illustrating another type of coupling mechanism that may be used to couple an electrode to the electrode patch of FIG. 15A.

FIG. 16 is a diagram illustrating another type of coupling mechanism that may be used to couple electrode 322 of FIG. 15 to electrode patch 239C. This diagram includes a portion of electrode patch 239C showing an aperture 350 to receive affixation device 326. A coupling device 352 is shown to receive, and to couple to, affixation device 326. For example, affixation device 326 and coupling device 352 could implement a snap-like mechanism. Coupling device 352 is further coupled to a lead 354 containing a conductor that will couple to a connector block such as connector block 340 of FIG. 15.

Figure 17:
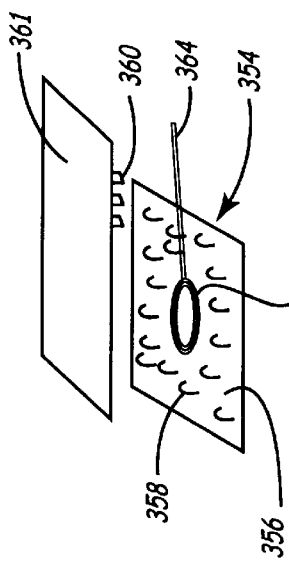
FIG. 17 is a diagram of another embodiment of an electrode that could be used with an electrode patch of FIG. 15A.

FIG. 17 is a diagram of yet another embodiment of an electrode that could be used with an electrode patch similar to that shown in FIG. 15. In this embodiment, electrode 354 includes at least a portion of a surface 356 having hook-like fixtures of the type that may affix to loops in an adjacent surface. Such loops 360 are shown provided on a portion 361 of a patch such as patch 239C. This is the type of hook-and-loop fastening system provided by a Velcro® brand material commercially available from Velcro Brand Fastening Systems. In this embodiment, patch 239C need not include apertures, but could instead include grid, angle, and/or distance markings to aid in positioning the electrodes. FIG. 17 further shows a connector 362 affixed to surface 256 of electrode 354. Connector 362 is electrically coupled to an electrode surface (not shown) on the reverse side of the electrode 354 that is adapted to be placed on a patient's skin. Connector 362 is further electrically coupled to a conductor carried in lead 364. Lead may be coupled to a connector block such as connector block 340 so that ECG measurements may be taken in the manner discussed above.

Figure 18:
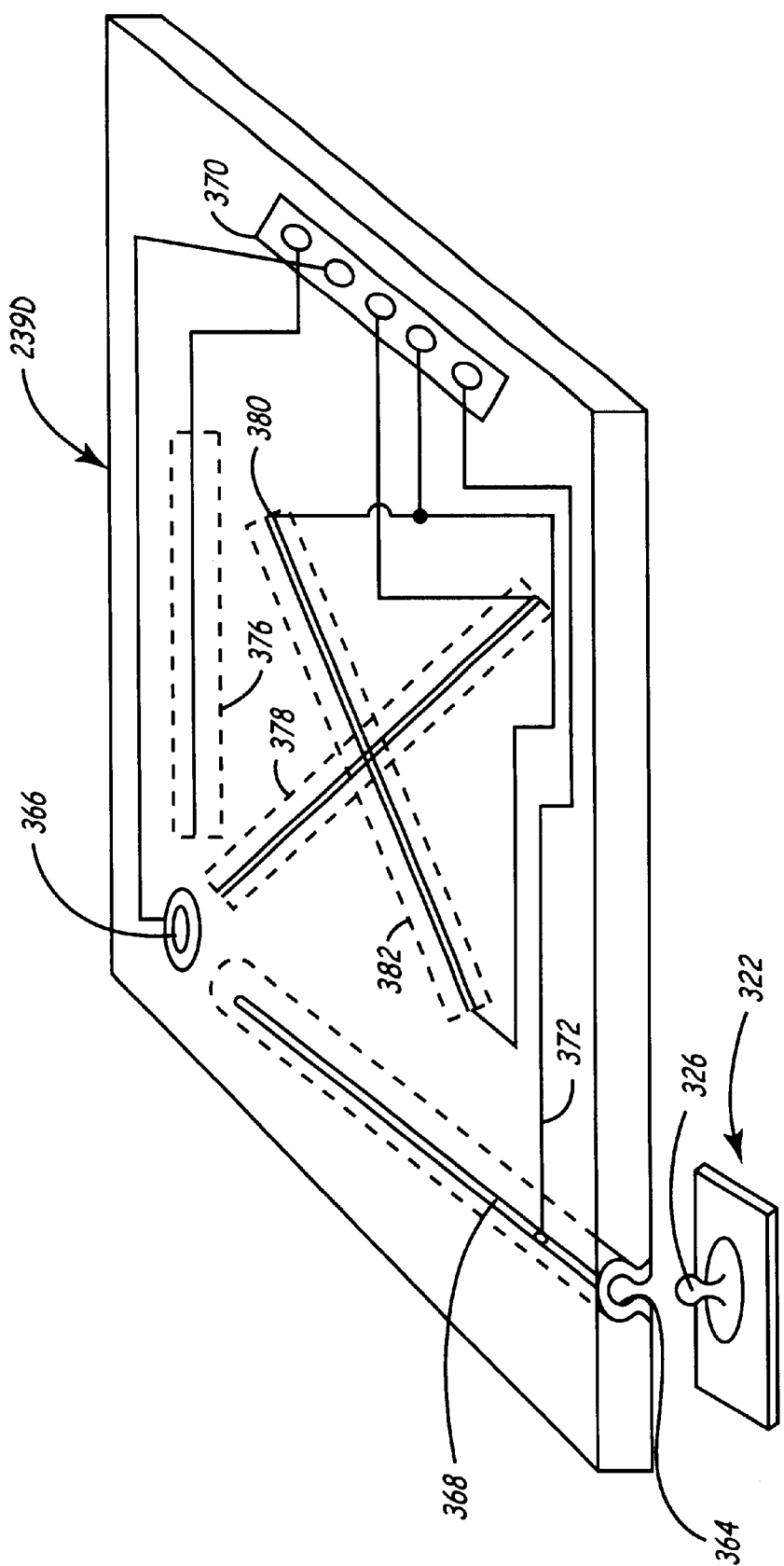
FIG. 18 is a diagram of an electrode patch having electrodes that may be slidably re-positioned on an electrode patch.

FIG. 18 is a diagram of an electrode patch having electrodes that may be slidably re-positioned on the patch. This figure shows electrode 322 having affixation device 326. In this embodiment, electrode patch 239D includes channels such as channel 364 adapted to slidably engage affixation device 326 so that the electrode 322 may be selectively positioned at a desired distance from a stationary coupling device 366. Channel 364 includes a conductive trace 368 to electrically couple to affixation device 326, which in turn couples to an electrode device on the opposite surface of electrode 322. Conductive trace 368 is further electrically coupled to conductor block 370 via trace 372 in a manner similar to that discussed above.

The stationary coupling device 366 is also adapted to receive an electrode, and is also coupled electrically to conductor block 370 via trace 374. As stated above, track 364 allows the electrode coupled within the track to be selectively positioned a desired distance from the electrode that is coupled to affixation device 366. Other tracks 376, 378, 380, and 382 (shown dashed) are also illustrated for receiving electrodes that may be slidably re-positioned to obtain a predetermined electrode-pair spacing. Each of the tracks includes a conductive trace that is electrically coupled to conductor block 370.

FIG. 19 is yet another implementation 239E of the electrode patch. In this embodiment, the electrodes are arranged in a circular pattern. Although eight electrodes 390 through 397 are shown to measure signal amplitudes having vectors A through D, any number of electrodes may be included. Any of the types of connection mechanisms and terminal configurations discussed above could be included in this embodiment.

FIG. 19 shows the electrodes 283A and 283B connected to two of the terminals included in connector block 398 of the electrode patch. In this embodiment, each of the vectors A through D is associated with two terminals, and the measurement to be taken is selected by re-positioning leads 283A and 283B to connect to the appropriate terminal pair. Many other types of selection mechanisms are available, however.

FIG. 20 is a diagram illustrating an electrode patch 239F that utilizes a sliding switch 399. Sliding switch includes a bar 400 that may be slidably re-positioned to select the vector to be measured. In this configuration, the ECG leads 283A and 283B remain connected to terminal connectors 402 and 404 throughout the measurement process, and only the bar must be moved when additional measurements are to be taken.

FIG. 21 is a diagram illustrating an alternative selection mechanism including a dial switch 406. The dial switch is shown positioned to select a signal having a vector A. The dial may be rotated to select measurement of a signal having a different vector B, C, or D. As in the sliding switch configuration discussed above, the ECG leads 283A and 283B remain connected to terminal connectors 408 and 410 throughout the measurement process.

Although the current invention is described above in the context of measuring cardiac signals, it will be understood that this invention is equally adaptable for measuring other physiologic electrical signals, and for determining optimal placement of other types of devices.

Non-Orthogonal Electrode Configurations

All of the above-described embodiments of the electrode patches contemplate the use of electrodes that are orthogonally-oriented with respect to each other. It may be noted that this is not a requirement. The commonly-assigned co-pending U.S. patent application Ser. No. 09/721,275 entitled "System and Method for Deriving a Virtual ECG Signal", filed on even date herewith, and which is incorporated herein by reference in its entirety, describes a system and method for utilizing three co-planar electrodes positioned in any orientation with respect to one another for measuring two physiologic signals S1 and S2. These signals may be used to approximate the amplitude of a third signal S lying within the plane of the electrodes. This approximation may then be used to select an orientation for the implantable medical device that corresponds with a desired morphology for the signal S.

Figure 27:
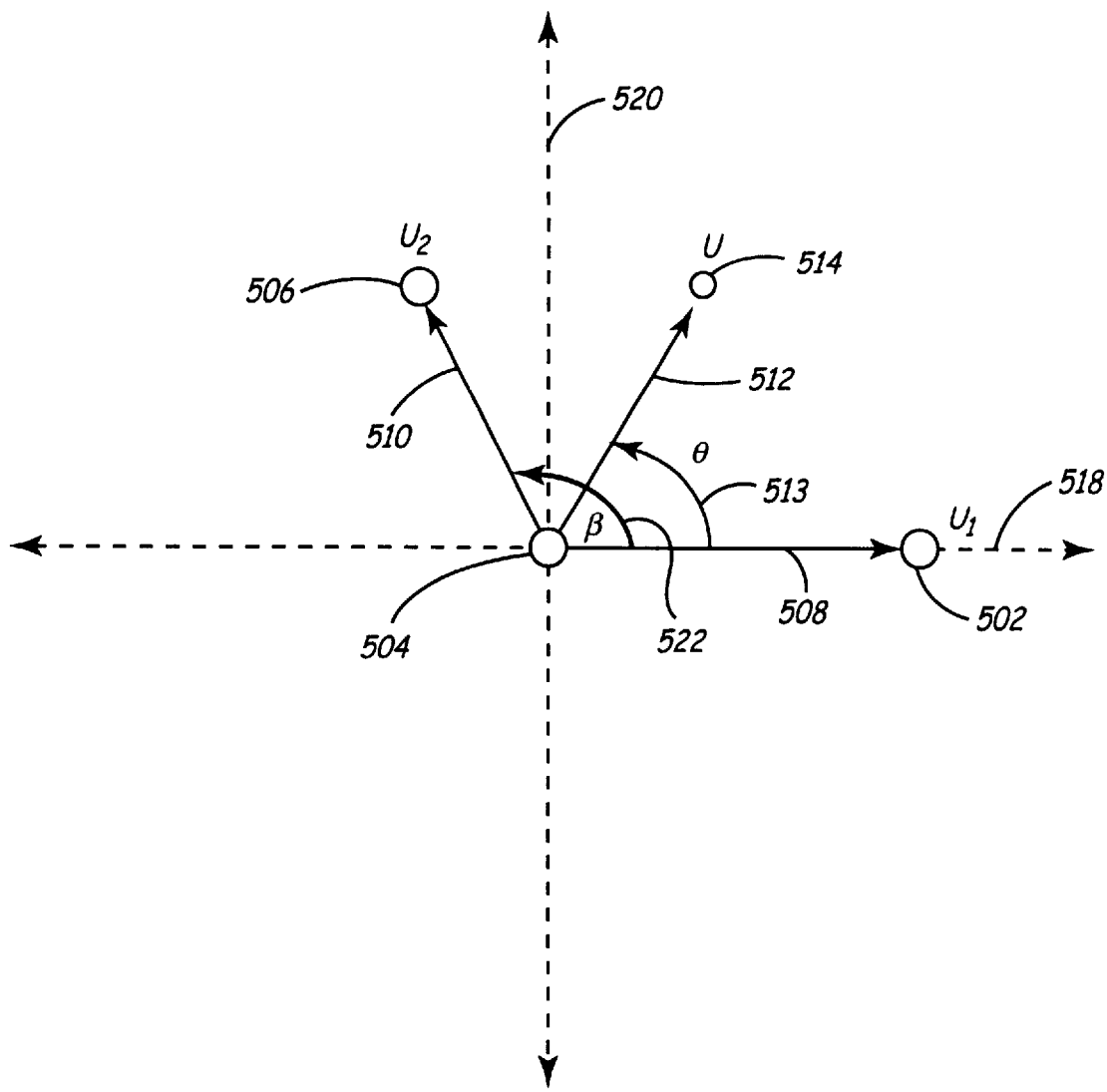
FIG. 27 is a diagram of an electrode configuration that utilizes electrodes oriented in a non-orthogonal relationship to approximate an optimal position for the implantation of an implantable medical device

FIG. 27 is a diagram of an electrode patch that utilizes electrodes oriented in a non-orthogonal relationship to approximate an optimal position for the implantation of an implantable medical device. The three electrodes 502, 504, and 506 may be positioned in any orientation with respect to each other. A first voltage potential S1 508 may be measured between electrode 502 and common electrode 504. A second voltage potential S2 510 may be measured between electrode 506 and common electrode 504. Using these measurements, an automated method may be employed to determine a virtual signal S 512. The signal S may have any arbitrary directional vector located within the plane defined by electrodes 502, 504, and 506. The orientation of this vector may be described using the angle θ 513. Studies have shown that this virtual signal S 512 as derived using actual signals S1 and S2 closely approximates the signal that would be measured between an electrode at position 514 that is a user-selectable distance D from the common electrode 504 as follows.

The method used to determine the virtual signal S is based on vector arithmetic principles. To illustrate, an X axis 518 and Y axis 520 (both shown dashed) may be super-imposed on FIG. 27, with the common electrode being positioned as the intersection of the X and Y axis. The X axis is shown coinciding with the direction of signal S1, although this is an arbitrary selection designed to simplify the following discussion. The signal S1 may now be described as having a directional vector U1 having coordinates of (1,0). Similarly, signal S2 may be described as having a directional vector U2 with coordinates of (cos β, sin β), wherein β 522 is the angle measured counter-clockwise between U1 and signal S2. Finally, the directional vector U of signal S may be described as having the coordinates (cos θ, sin θ), wherein θ is the angle measured counter-clockwise between U1 and signal S.

According to the principles of vector arithmetic, the directional vector U may be defined as a function of the two directional vectors U1 and U2 as follows:

$$U=(A \times U1)+(B \times U2)$$

wherein A and B are scalar parameters that are functions of the selected angle θ and the angle β. Using matrix algebra, this equation may be re-written as follows:

$$\begin{pmatrix} \cos\theta \\ \sin\theta \end{pmatrix} = \begin{bmatrix} 1 & \cos\beta \\ 0 & \sin\beta \end{bmatrix} \begin{pmatrix} A \\ B \end{pmatrix}$$

Solving this equation for A and B results in the following:

$$A = \sin(\beta-\theta)/\sin\beta; \text{ and}$$

$$B = \sin\theta/\sin\beta$$

Recall that S1 and S2 are the voltage signals measured empirically between the respective electrode pairs having the directional vectors of U1 and U2, respectively. Using the voltage measurement S1, the electric fields existing between the first pair of electrodes 502 and 504 may be defined as $$E1 = S1/D1,$$

wherein D1 is the distance between electrodes 502 and 504. Similarly, the electric field measured between the second pair of electrodes 504 and 506 may be defined as $$E2 = S2/D2,$$

wherein D2 is the distance between electrodes 504 and 506.

It is known that these two electric fields can be used to approximate the electric field E having the direction vector U between electrode 504 and the selected point 514. The approximation of this electric field may be expressed as follows:

$$E=(A\times E1)+(B\times E2),$$

where A and B are the scalar parameters discussed above.

Making a series of substitutions, the following is derived for E:

$$E=(A\times S1/D1)+(B\times S2/D2)$$

$$E=((\sin(\beta-\theta)/\sin \beta)\times(S1/D1))+((\sin \theta/\sin \beta)\times(S2/D2))$$

Finally, recall that the approximated voltage signal S between the electrode 504 and the point 514 may be described as a function of the electric field E existing between these two points and the electrode spacing D as follows:

$$S=D\times E,$$

wherein D is the distance between the electrode 504 and point 514.

Thus, S may be expressed as:

$$S=D\times[((\sin (\beta-\theta)/\sin \beta\times(S1/D1))+((\sin \theta/\sin \theta\times(S2/D2))],$$

or $$S=(D/\sin \beta)\times[\sin \beta-\theta)\times(S1/D1))+(\sin \theta\times S2/D2)]$$

Using this description, a close approximation of the amplitude of the signal S may be determined wherein S is the signal that would be measured between electrode 504 and a second electrode positioned at location 514, wherein this selected location 514 is a distance D from electrode 504. In the preferred embodiment, location 514 will be selected such that distance D is fixed at some value between D1 and D2, with D1 and D2 being of relatively the same size. This allows for a better approximation of the signal S when adding the electrical fields associated with the two electrode pairs.

The distance D is a scale factor that does not change the morphology of the time-varying signal S. In that respect, the D can be selected to scale the amplitude of the time-varying signal to the voltage range dictated by circuit requirements. For example, D can be thought of as a programmable amplifier gain that is selected to best allow the signal to be converted by a standard analog-to-digital converter to digital format. In one embodiment, this value is not variable, but is fixed based on circuit requirements and the desired amplitude of the signal S.

Functional Considerations Associated with Leadless Implantable Sensing Devices

FIG. 3 illustrates an external device 30A that is often referred to as a "programmer" in the pacemaker art, because it's usual function is to communicate with, and to program, implanted devices. Software modifications and modifications to the telemetry system of device 30A to accommodate communication with and analysis of data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for ECG monitoring and event triggering is minimal, so in the preferred embodiments that only monitor some form of ECG or other limited sensory input, a microprocessor may be eliminated by using particularized functional circuits instead of doing the functions in software.

Figure 3A:
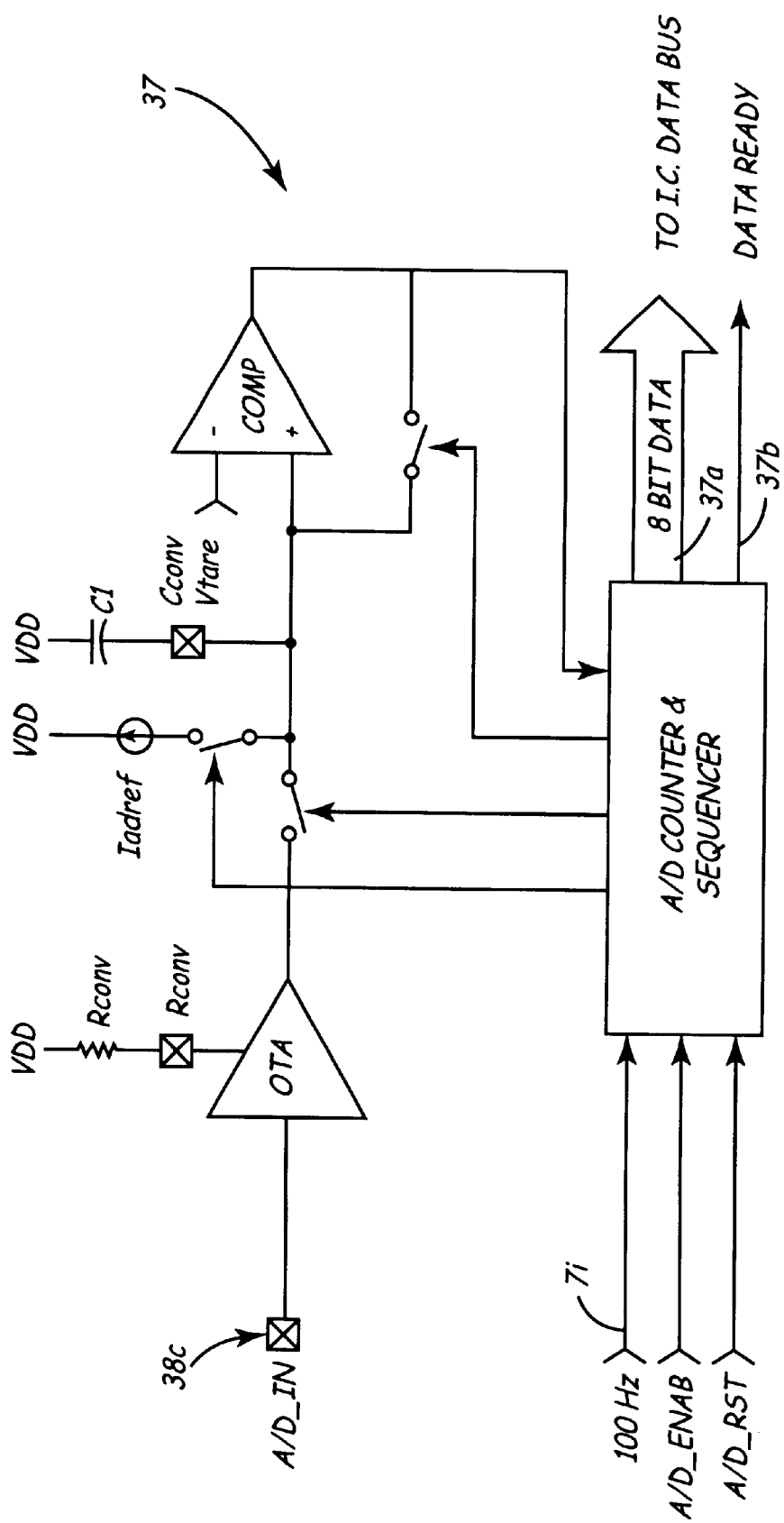
FIGS. 3A–D are block diagrams of preferred embodiment circuits of the implanted device used for monitoring and storing ECGs.

In FIG. 3A, a block diagram of an analog to digital conversion circuit for use in this invention is shown. The clock input may advantageously use an output from the clock circuit 7, input 7i. The input 38c is the analog input signal from input circuit 38, and the converted output is a stream of 8 bit digital data words on line 37a, sequenced by a timing line 37b.

Figure 3B:
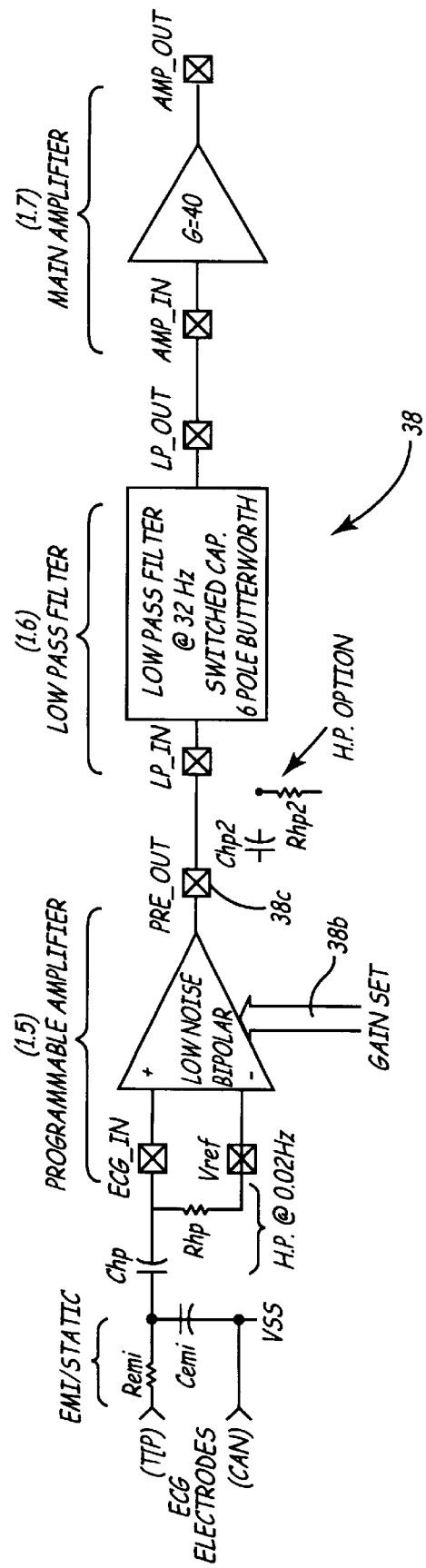

FIG. 3B illustrates the basic parts of circuit 38, additionally indicating the input of gain set bits which can modify the value of the output of the low noise bipolar amplifier for output at line 38c, the input to the QRS detector. In this invention QRS detection is done on the analog signal, advantageously saving more complex detection after digital conversion.

Figure 3C:
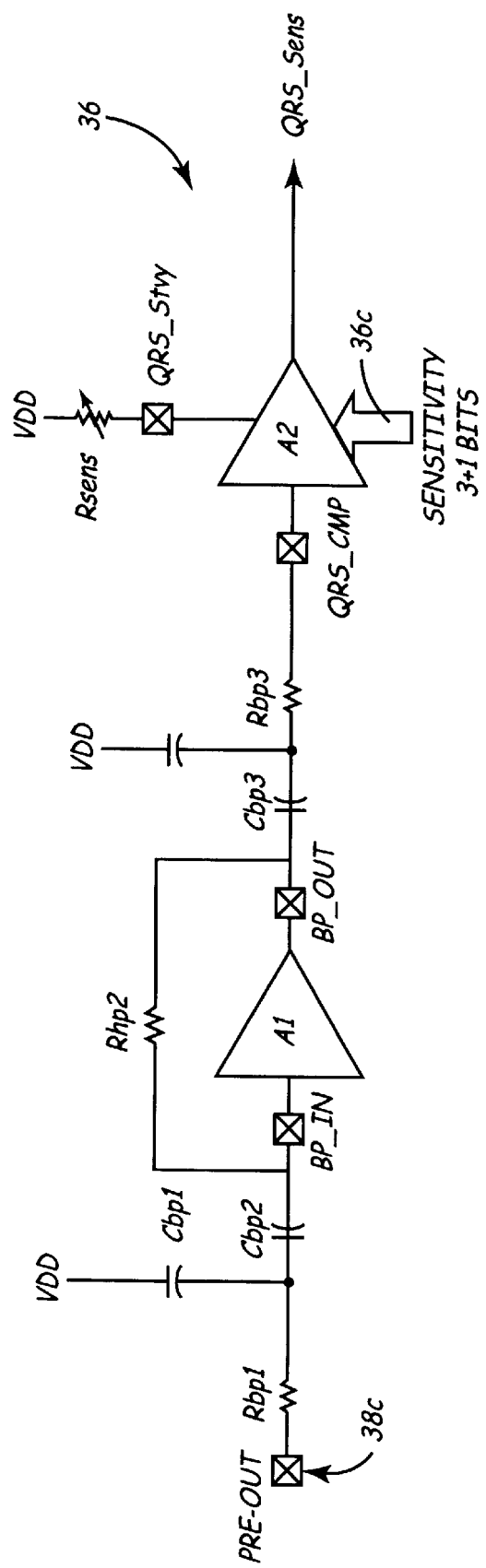

In FIG. 3C, QRS detect circuit 36 has a 2nd order bandpass filter with a center frequency preferably in the 20–25 Hz range. It includes a transconductance amp A1, summing amp/comparitor A2 and resistors Rbp 1–3, capacitors Cbp 1–4 and selectable resistor R sense connected as shown. R sense is preferably adjusted during manufacture. Additional control is provided for QRS sensitivity at line 36c, since the gain is delectable for this input.

Figure 3D:
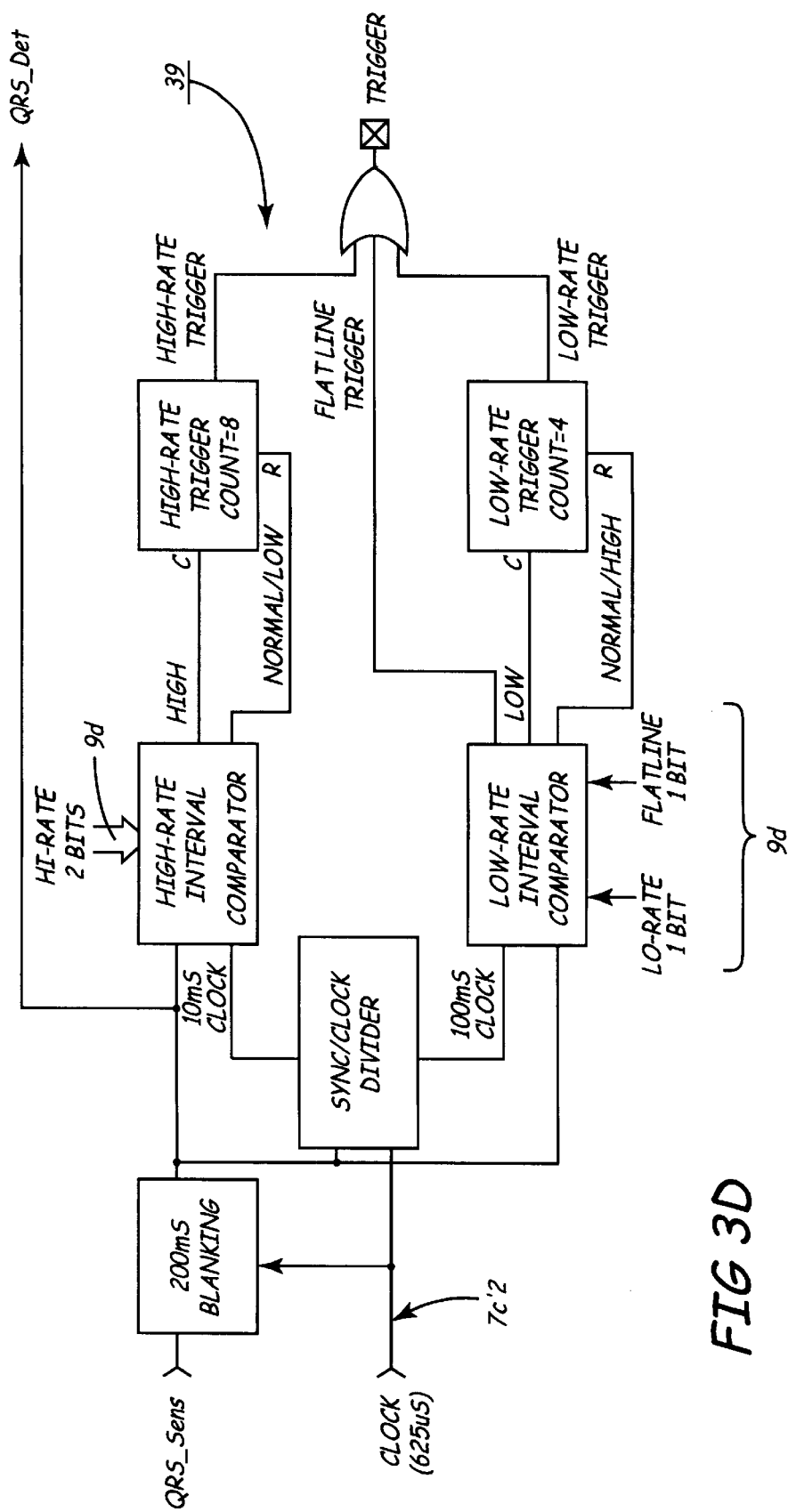

A simple arrhythmia detection circuit 39 is included with this preferred embodiment, and illustrated in FIG. 3D. The output from circuit 36 is monitored at a 200 millisecond blanking interval circuit, controlled by a clock input 7i2. In the preferred embodiment, a high rate can be selected amongst 4, with two selection bits dedicated to do so at input 9d and the low and flatline trigger rates each have one bit to turn them on or off provided by inputs 9d. These inputs designated 9d preferably come from a register that holds the gain the mode and the rate settings, illustrated as register 9 in FIG. 3. Such features may be programmable through communication with the implanted device by an external device. Preferred timing for the high rate triggers is 140, 162 and 182 beats per minute, requiring 8 consecutive beats at such a rate to initiate the trigger. Additionally the trigger may be programmed off. The low rate counter/comparitor may be programmable to detect low rates of 40 or 30 bpm, requiring 4 consecutive low rate intervals to trigger. Additionally a flat-line trigger can be set to occur after 3 or 4 and one half seconds of no QRS detection.

For embodiments that include more sensors and/or electronics, an additional sensor could be added to benefit the patient. For example, an activity sensor may be provided that is based on a single or multi-axis accelerometer, and that indicates the level of patient activity and his orientation. By checking for output that indicates the occurrence of a VVS (VasoVagal Syncope) episode, (for example, the patient falling from an episode) such an addition offers an improved trigger for events that might otherwise be missed by an arrhythmia detector set up like in FIG. 3D. Such a sensor trigger could replace the circuitry of 3D.

Additional circuits may be provided to support additional functions if desired, however in order to reduce size and power consumption and extend the life of the device and reduce the intrusion into the body of the wearer, auxiliary circuits should be kept to a minimum. Such additional circuits could support oxygen sensing, pressure sensing, respiration sensing, and any other kind of sensing that can be demonstrated to have been known for implanted devices. They may each have their own auto triggers based on sensor output, or depend on manual triggers. Additionally, activity sensing or positional sensing devices can provide additional input for recordation and or auto-triggering functions. As new sensors become available they may also be incorporated into these designs.

In considering size, the maximum dimension of the device need be only the minimum required dimension for good signal to be obtained from the two electrode areas. In our studies we have found useable signal for ECG monitoring at a distance of about ½ inch(1 cm). The best minimum electrode distance for current electronics at reasonable prices appears to be from ¾ inches to 2 inches.

ECG Recording Functionality for Preferred Embodiments

The most important function of the simple versions of this invention is the long term ECG monitoring of the subcutaneous (or intramuscular) ECG. The device continuously records and monitors the subcutaneous ECG in an endless loop of memory. In its primary mode the device is triggered to save/retain in memory the last X minutes or seconds of ECG data by the patient subsequent to feeling symptoms of interest (e.g. syncope, palpitations, etc.).

In the preferred embodiment with 128K of memory the device can store 42 or 21 minutes of ECG, which can be reset after offloading by telemetry to an external device for analysis and display. In one form there are four modes settable for patient trigger only and in another form there are autotriggers. In the patient only(also called "manual")trigger modes, the patient can capture either one or three events between offloadings at either no compression or at a compression ratio of 1:2 or some other device supported ratio. When setting the mode of the implant, the physician or attendant can decide whether to record data in a compressed mode or not in the preferred embodiment. If greater detail of the triggered ECG is required than can be developed from compressed data storage, the physician should select non-compressed recording, thereby limiting the time available to record. In some embodiments sample rate may be modified as well, but this is not preferred.

Compression is preferably done using a known compression algorithm implemented in hardware. Many types are known and software compression could be used if desired too. An excellent and easy to implement example is found in the article Arrhythmia Detection Program for an Ambulatory ECG Monitor by Mueller, copyright 1978, ISA, ISBN 876645. Using this algorithm in one embodiment we have used a pre-trigger time of record of a maximum of 2400 seconds and a maximum post trigger record of 120 seconds, and at the higher sampled or less compressed rate of 1200/60 for a single event and 360/60 seconds for three events. These time values are obviously only examples and the reader can set whatever time the or his physician feels is appropriate within the ambit of this invention. After such a record is made the device memory locations are full and will be overwritten by the next triggered event since in the preferred embodiment the memory is maintained in a continuous loop.

Additional modes include those with pure auto-triggering, which can mirror the patient triggered only modes if desired. It should be considered that with auto-triggered events, the determination by the device of an event worth recording and the subsequent activation of the trigger by the device itself will be faster than the patient finding his device for activation or otherwise activating the device, so the pre trigger time record can be smaller. In one preferred embodiment the memory is segmented to allow for 14 auto-triggers and 3 manual triggers. Further detail regarding modes is described with reference to FIGS. 19 and 20.

The patient activated triggering of a preserved form of the recorded ECG signal can be carried out by using a small handheld external device which may be of any number of different forms. A first way is through a handheld battery-powered device which uses a coded radio-frequency telemetered signal through the skin to the device, on the press of a button. A simpler device a small handheld used to close a magnetic switch within the implanted device to trigger it by holding the magnet close or patting the area of the body that has the implant a set number of times with the magnet. Other methods for triggering ECG data retention in memory (each of which has it's own advantages for implementation) are to use physical tapping or slapping of the finger or hand on the skin over the device in a particular cadence and/or number of taps (advantage is that no triggering device is needed. With such methods the disadvantage is that the patient needs to memorize the triggering sequence. Matched voice activation with a known command is possible but the complexity at this time of discerning voice commands precludes such activation for the present time, but could be in future devices using this invention. Another approach is light activation through the skin using a light source and receiver, auditory/sonic activation using a handheld auditory/sonic source held over the skin with a microphone receiver in the device. All these methods are patient activated and require patient compliance or cooperation, a feature this device was designed to avoid. Accordingly in conjunction with one of these patient triggers or alone, an automatic activation or trigger for holding a chunk of memory should be included. This could be activated by automatic recognition of an arrhythmia, a heartbeat too fast or too slow, or for any other condition the device may be set up to find.

If a patient trigger is used it is advantageous provide feedback to the patient regarding whether the attempt to trigger long term storage of the event was successful. To accomplish this the implant should telemeter out a signal that indicates it has recognized a valid trigger. (This of course requires additional circuitry and usage of the limited available power supply.) The external triggering device then notifies the patient via the triggering device or through some known alarm mechanism whether they have or have not properly triggered the implanted device. This notification can be one of any combination of a number of feedback methods including: one or two visual sources such LED's, an auditory source such as a beeping speaker in one or two tones, or a tactile source such as a vibration. See also U.S. Pat. No. 5,518,001 for other potential trigger-indicator ideas for a hand-held patient activated trigger device.

Features and Construction of the Preferred Embodiment of Implantable Devices

Figure 22:
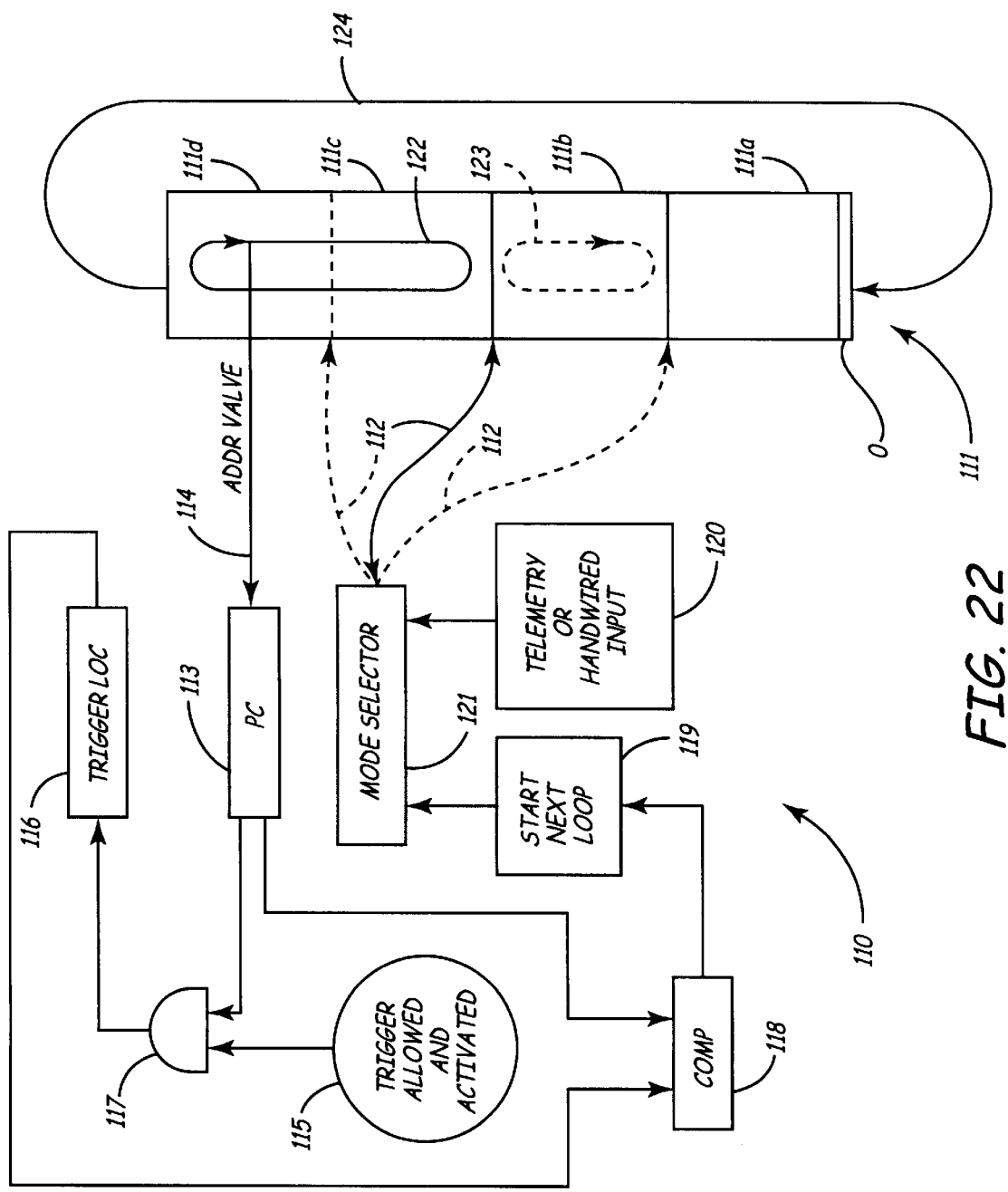
FIG. 22 is a block diagram of the looping memory and its control circuitry in accord with a preferred embodiment of an implantable sensing device.

Referring now to FIG. 22 in which a block diagram of a functional model 110 of the controller and memory 111 of a preferred embodiment device is illustrated. The memory is generally organized as a continuous loop of, preferably, 8 bit addresses starting at address 0 and looping back around to address 0 through line 124. By telemetry or hard-wired input during manufacture 120, a mode selector 121 is set so as to divide the memory 111 into working segments 111a–d. The address of the start of each of these segments is indicated with lines 112.

Since this device is used for recording physiologic data, after the data is compressed, converted, formatted and is in appropriate digital form, it is continually recorded in the memory 111. The address value at the tip of arrow 122 in the combined memory space 111d, 111c is monitored by a program counter register 113.

The size of each memory segment set in a given mode limits the amount of data available for each triggered event. In the preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7.

To use a single program counter the actual trigger address minus the time (in memory location storage events) required to have already stored the amount of data needed for pre event analysis for that trigger is stored as a value in the trigger location register 116 of FIG. 22. If a larger time for pre trigger recording is required by a trigger occurring during an already triggered event,(say, a manual trigger follows the occurrence of an auto trigger), the value in the trigger register can be decremented, thus yielding a larger pre trigger time period in the allocated memory segment for this event. A priority system for whether to extend the pre trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto triggered one because upon recovering from an event the patient has enough time to recover, get their wits about them, and find the triggering device. Manual triggering may therefore be set to record in double or multiple sized segments. Segments 111c and d are joined by looping arrow 122 to give effect to this concept.

Because the memory size is preferably quite limited a time record or first-in-first-out pool record should be kept on order that the newest triggers record only over the oldest events segments. An additional preferred feature allows for a mode that prevents recording over any triggered event segment. This is preferably implemented by a counter which fills for each segment used and has storage for the set number of looping segments. When it is full recording of new events stops.

When a trigger is activated and under the control program of the device is allowed, a signal 115 is permitted by some control gate 117 to allow the program counter address to be loaded into a trigger location address register 116. After loading, each subsequent clock cycle or set of clock cycles depending on the configuration of the device will load the trigger location from 116 into a comparator 118 to compare this location with the program counter address stored in register 113. When comparator 118 finds that they match, an appropriate output is generated to start the next loop via control circuit 119. This control circuit 119 will cause the mode selector to point to the next available loop location effectively placing that into the program counter 113.

Figure 23:
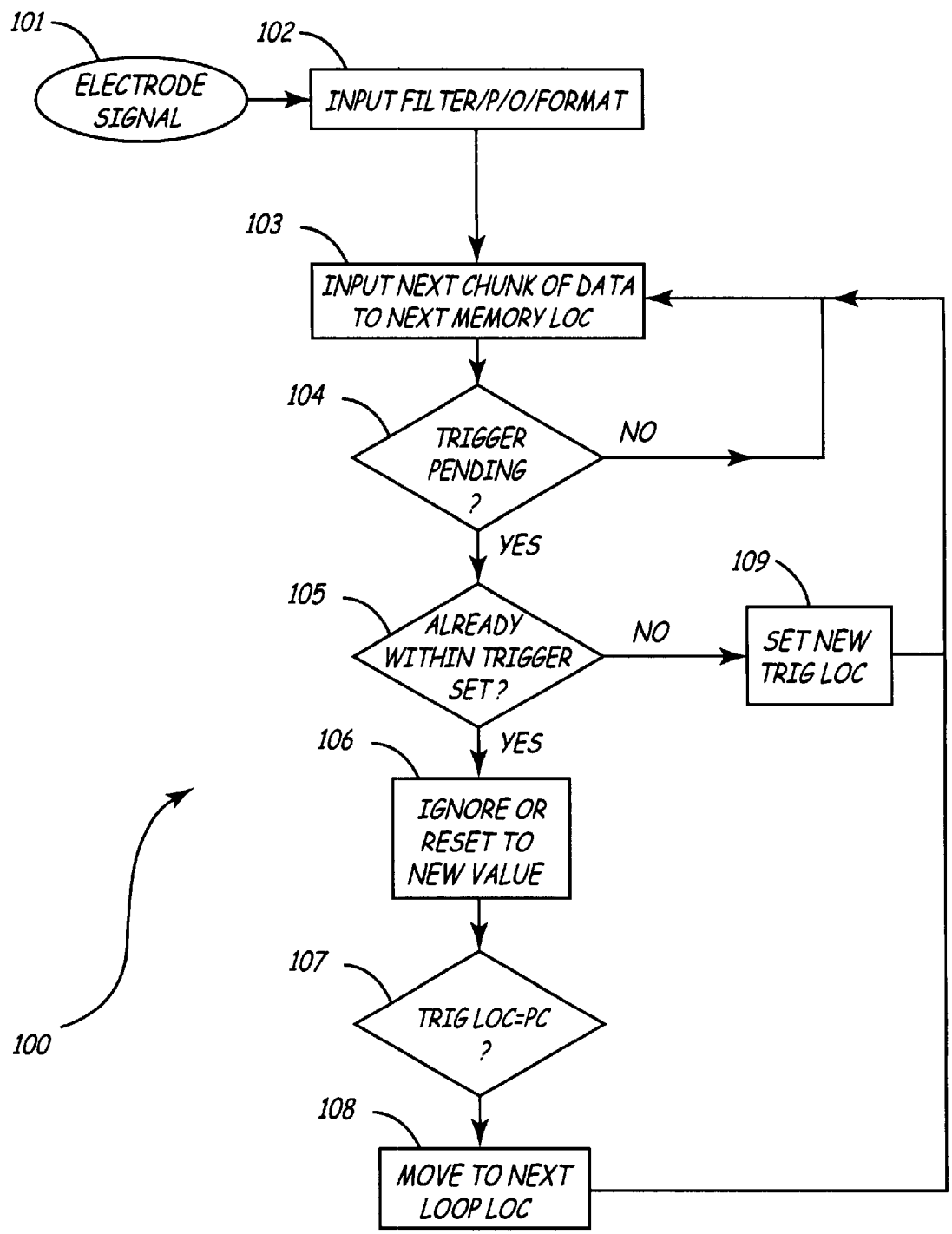
FIG. 23 is a flow chart of the functioning of the recordation of triggered events in a preferred embodiment of the invention.

The method 100 to indicate the flow of this information is found in the illustration of FIG. 23 in which an electrode signal 101 is input filtered, converted from analog input to digital values, compressed and formatted if desired in step 102 so as to be in appropriate form to store in a memory location designated by a program counter pointer.

This data word's form could be containing a value representing input signal compressed at various available ratios, and may be mixed with other information like data provided by another sensor or clock data. The data stored will of course carry information related to the signal taken at the sampling rate. Thus lower sampling rates to save power will adversely affect the usefulness or detail of the data. Whatever its preferred form, each data point stored as a word is referred to as a chunk.

Output form step 102 provides the next portion of data to the next memory location in step 103.

Device checks to see if there is any trigger pending after storing each portion of data in step 104. If not, the next portion of data is stored. If there is, the device preferably checks to see if there is another trigger already set and if so either ignores it or resets the value of the reserved looping memory area (like areas 111a–d in FIG. 22) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

It should be recognized that any of the inventive concepts taught herein may be applied to implantable devices to supplement other functions, such as a supplemental recording system for a pacemaker, or an implantable drug pump. Further, although the invention is discussed herein with reference to the measurement of cardiac signals, it will be understood that other types of physiological signals may be measured by the inventive system and method. Further, known enhancements to telemetric communication can be used to automatically activate offloading of data to a device located in the patient's home. Such a device could send its received communications to the attending care giver/physician's office at some convenient time, telephonically or otherwise so as to enable close compliance with prescribed follow-up of patient conditions. Therefore, this invention is not understood to be limited in scope except by the following claims.

What is claimed is:

1. A system for determining an optimized orientation of an implantable device within a body, comprising:
   at least three electrodes, each positioned to contact an external surface of the body,
   means for utilizing the at least three electrodes to obtain at least two signal amplitude measurements, each between two predetermined points on the external surface; and
   means for determining the optimized orientation of the implantable device within the body using the at least two signal amplitude measurements.

2. The system of claim 1, wherein the means for obtaining includes:
   means for measuring a first signal amplitude between a first pair of the electrodes;
   means for measuring a second signal amplitude between a second pair of the electrodes; and
   processing means for deriving a first optimal angle of placement of the implantable device at a first location from the first and second signal amplitudes.

3. The system of claim 2, and including at least five electrodes, and further including means for measuring at least a third and fourth signal amplitude between a third and fourth pair of the at least five electrodes, respectively and wherein the processing means includes means for deriving at least a second optimal angle of placement of the implantable device at a second location from the third and fourth signal amplitudes.

4. The system of claim 3, wherein the processing means includes means for interpolating between the first and second optimal angles of placement to derive a third optimal angle of placement at a third location intermediate the first and second locations.

5. The system of claim 1, wherein the means for determining includes a processing circuit.

6. The system of claim 5, wherein the means for obtaining includes a selection circuit coupled to the processing circuit to allow the processing circuit to enable signal measurement between selected pairs of the at least two electrodes.

7. The system of claim 1, wherein the means for obtaining includes an ECG monitoring device.

8. The system of claim 7, wherein the ECG monitoring device is a hand-held device, and wherein the at least two electrodes are positioned on a predetermined surface of the ECG monitoring device.

9. The system of claim 8, wherein the ECG monitoring device includes means for allowing ones of the at least two electrodes to be re-positioned with respect to each other.

10. The system of claim 1, and further including a patch coupled to the at least two electrodes, the patch to be positioned on the external surface of the body.

11. The system of claim 10, wherein the at least two electrodes includes an array of electrodes arranged in a substantially circular pattern on the patch.

12. The system of claim 10, wherein the patch includes multiple affixation devices to allow the at least two electrodes to be coupled at selectable locations on the patch.

13. The system of claim 12, wherein at least one of the multiple affixation devices allows at least one of the electrodes to be slidably re-positioned to selectable locations on the patch.

14. The system of claim 10, wherein the patch includes Velcro to couple to ones of the at least two electrodes.

15. The system of claim 1, wherein the circuit to measure signal amplitudes includes an ECG monitoring device.

16. The system of claim 15, wherein the ECG monitoring device is a hand-held device, and wherein the at least two electrodes are positioned on a predetermined surface of the ECG monitoring device.

17. The system of claim 16, wherein the ECG monitoring device includes means for allowing ones of the at least two electrodes to be re-positioned with respect to each other.

18. A method of determining an optimal position of an implantable device within a body, comprising the steps of:
   a.) taking at least two signal measurements, each between a respective pair of electrodes positioned on the body;
   b.) using the at least two signal measurements to determine the optimal placement position of an implantable device within the body, where step a.) includes positioning multiple electrode pairs on the surface of the body and enabling selected ones of the multiple electrode pairs to take the at least two signal measurements.

19. The method of claim 18, wherein enabling selected ones of the multiple electrode pairs to take the at least two signal measurements includes automatically enabling selected ones of the multiple electrode pairs by enabling an electronic switching circuit.

20. The method of claim 18, wherein step a.) is performed using an ECG monitoring device.

21. The method of claim 20, wherein the ECG monitoring device is handheld and includes at least one pair of electrodes selectively positioned on a surface of the handheld ECG monitoring device, and wherein step a.) includes positioning the surface of the handheld ECG on the surface of the body.

22. The method of claim 21, further comprising the step of re-positioning the at least one pair of electrodes on the surface of the handheld ECG monitoring device.

23. The method of claim 21, wherein step a.) further comprises the step of obtaining the at least two signal measurements using a user display provided by the handheld ECG monitoring device.

24. The method of claim 21, wherein step a.) further comprises the step of storing the at least two signal measurements in a memory device included in the handheld ECG monitoring device.

25. The method of claim 23, wherein the step of storing further comprises the step of transferring stored ones of the at least two signal measurements to a device that is external to the handheld ECG monitoring device.

26. The method of claim 18, wherein step a.) comprises the steps of:
   a1.) taking a first signal measurement B between a first electrode pair;
   a2.) taking a second signal measurement A between a second electrode pair that is orthogonally-positioned with respect to the first electrode pair; and
   a3.) using the measurements A and B to determine a first optimal angle of placement of the implantable device.

27. The method of claim 26, wherein step a3.) includes determining the first optimal angle of placement for the implantable device that is the Arc-Tangent(B/A), wherein the optimal angle is measured from the second electrode pair.

28. The method of claim 26, further comprising the steps of:
   a4.) taking a third signal measurement C between a third electrode pair;
   a5.) taking a fourth signal measurement D between a fourth electrode pair; and
   a6.) using the measurements C and D to determine a second optimal angle of placement of the implantable device.

29. The method of claim 28, further comprising the step of using extrapolation to determine a third optimal angle of placement from the first and second optimal angles of placement.

30. The method of claim 28, wherein step a6.) includes determining the second optimal angle of placement for the implantable device that is the Arc-Tangent(D/C).

31. The method of claim 18, wherein step a.) is performed using an electrode patch that is coupled to at least one pair of electrodes.

32. The method of claim 31, wherein the electrode patch includes means for re-positioning the at least one pair of electrodes on the patch, and wherein step a.) further comprises the step of adjusting the spacing between the electrodes included in the at least one pair of electrodes.

33. The method of claim 31, further comprising the step of selecting electrodes of a size that will accurately determine the optimal position.

34. The method of claim 31, wherein step a.) includes re-positioning the patch to at least one new location on the body.

35. The method of claim 31, wherein the patch includes a connector block, and step a.) further comprises the step of selectively enabling the at least one pair of electrodes by electrically coupling the at least one pair of electrodes to the connector block.

36. The method of claim 18, wherein step b.) is performed by determining an optimal directional vector U at which a maximum signal amplitude S may approximately be measured, and wherein the maximum signal amplitude S is determined as a function of:
   b1.) the amplitudes S1 and S2 of the at least two signal measurements;
   b2.) an angle β between the directional vectors of the two of the at least two signal measurements; and b3.) distances D1 and D2 existing between a respective pair of electrodes used to measure S1 and S2, respectively.

37. A system for determining an orientation of an electrode pair in order to obtain a maximum physiological signal from a surface of a body, comprising:

at least two electrodes, each positioned to contact the surface of the body, a circuit to measure signal amplitudes between predetermined pairs of the at least two electrodes; and a circuit to determine an orientation on the surface of the body at which a pair of the at least two electrodes may be positioned to obtain a maximum signal amplitude.

38. The system of claim 37, wherein the circuit to measure signal amplitudes measures a first signal amplitude between a first pair of the electrodes, measures a second signal amplitude between a second pair of the electrodes, and the circuit to determine an orientation derives a first optimal angle of orientation at a first location from the first and second signal amplitudes.

39. The system of claim 38, wherein the circuit to measure signal amplitudes measures at least a third and fourth signal amplitude between a third and fourth pair of the electrodes, and the circuit to determine an orientation derives a second optimal angle of orientation at a second location from the third and fourth signal amplitudes.

40. The system of claim 39, wherein the circuit to determine an orientation interpolates between the first and second optimal angles of placement to derive a third optimal angle of placement at a third location intermediate the first and second locations.

41. The system of claim 37, further comprising a patch coupled to the at least two electrodes, the patch to be positioned on the external surface of the body.

42. The system of claim 41, wherein the at least two electrodes includes an array of electrodes arranged in a substantially circular pattern on the patch.

43. The system of claim 41, wherein the patch includes multiple affixation devices to allow the at least two electrodes to be coupled at selectable locations on the patch.

44. The system of claim 41, wherein at least one of the multiple affixation devices allows at least one of the electrodes to be slidably re-positioned to selectable locations on the patch.

45. The system of claim 41, wherein the patch includes Velcro to couple to ones of the at least two electrodes.

* * * * *